(12) United States Patent
Kislev et al.

(10) Patent No.: US 10,779,946 B2
(45) Date of Patent: Sep. 22, 2020

(54) LEAFLET-TESTING APPARATUS

(71) Applicant: CARDIOVALVE LTD., Or Yehuda (IL)

(72) Inventors: Yonatan Kislev, Rosh Haayin (IL); Or Cohen, Tel Aviv (IL); Meni Iamberger, Kfar Saba (IL)

(73) Assignee: CARDIOVALVE LTD. (IL)

( * ) Notice: Subject to any disclaimer, the term of this patent is extended or adjusted under 35 U.S.C. 154(b) by 179 days.

(21) Appl. No.: 16/132,937

(22) Filed: Sep. 17, 2018

(65) Prior Publication Data

US 2020/0085578 A1 Mar. 19, 2020

(51) Int. Cl.
*A61F 2/24* (2006.01)

(52) U.S. Cl.
CPC .......... *A61F 2/2472* (2013.01); *A61F 2/2415* (2013.01)

(58) Field of Classification Search
CPC ................................ A61F 2/2472; G01L 1/24
See application file for complete search history.

(56) References Cited

U.S. PATENT DOCUMENTS

| | | | |
|---|---|---|---|
| 4,972,494 A * | 11/1990 | White | B65B 19/28 209/535 |
| 5,776,140 A | 7/1998 | Cottone | |
| 5,957,949 A | 9/1999 | Leonhardt et al. | |
| 6,010,530 A | 1/2000 | Goicoechea | |
| 6,245,105 B1 | 6/2001 | Nguyen et al. | |
| 6,402,780 B2 | 6/2002 | Williamson, IV et al. | |
| 6,413,275 B1 | 7/2002 | Nguyen et al. | |
| 6,837,902 B2 | 1/2005 | Nguyen et al. | |
| 7,585,321 B2 | 9/2009 | Cribier | |
| 8,361,144 B2 | 1/2013 | Fish et al. | |
| 8,628,571 B1 | 1/2014 | Hacohen et al. | |
| 8,728,155 B2 | 5/2014 | Montorfano et al. | |
| 8,850,898 B2 | 10/2014 | Johnsen | |

(Continued)

FOREIGN PATENT DOCUMENTS

| EP | 1264582 A2 | 12/2002 |
|---|---|---|
| WO | 1998/043557 | 10/1998 |

(Continued)

OTHER PUBLICATIONS

PCT International Search Report and a Written Opinion dated Nov. 9, 2018, in corresponding Application No. PCT/IL2018/050869, 19 pages.

(Continued)

*Primary Examiner* — Joshua L Schwartz
(74) *Attorney, Agent, or Firm* — Dilworth IP, LLC

(57) ABSTRACT

Embodiments of the present disclosure provide an apparatus for testing a plurality of prosthetic heart valve leaflets. The apparatus includes a vertical mount, and a plurality of horizontal bars are movably coupled to the mount. Each bar extends away from the mount along a respective bar-axis that lies on a respective vertical bar-plane. Each bar is configured to support a respective leaflet along the respective bar-axis such that the respective leaflet drapes over the respective bar. The apparatus further includes an image sensor, positioned opposite the mount, facing the plurality of bars and the mount so as to be oriented to acquire an image that includes the plurality of leaflets draped over the plurality of bars. Other embodiments are also described.

77 Claims, 16 Drawing Sheets

(56) References Cited

U.S. PATENT DOCUMENTS

| | | | |
|---|---|---|---|
| 8,852,272 B2 | 10/2014 | Gross et al. |
| 8,870,948 B1 | 10/2014 | Erzberger et al. |
| 8,998,982 B2 | 4/2015 | Richter et al. |
| 9,023,100 B2 | 5/2015 | Quadri et al. |
| 9,095,434 B2 | 8/2015 | Rowe |
| 9,097,620 B2 | 8/2015 | Caron et al. |
| 9,180,009 B2 | 11/2015 | Majkrzak et al. |
| 9,232,995 B2 | 1/2016 | Kovalsky et al. |
| 9,241,791 B2 | 1/2016 | Braido et al. |
| 9,241,792 B2 | 1/2016 | Benichou et al. |
| 9,248,014 B2 | 2/2016 | Lane et al. |
| 9,387,078 B2 | 7/2016 | Gross et al. |
| 9,439,757 B2 | 9/2016 | Wallace et al. |
| 9,492,273 B2 | 11/2016 | Wallace et al. |
| 9,554,899 B2 | 1/2017 | Granada et al. |
| 9,561,103 B2 | 2/2017 | Granada et al. |
| 9,662,203 B2 | 5/2017 | Sheahan et al. |
| 9,763,657 B2 | 9/2017 | Hacohen et al. |
| D800,908 S | 10/2017 | Hariton et al. |
| 9,788,941 B2 | 10/2017 | Hacohen |
| 9,895,226 B1 | 2/2018 | Harari et al. |
| 10,010,414 B2 | 7/2018 | Cooper et al. |
| 10,143,552 B2 | 12/2018 | Wallace et al. |
| 10,149,761 B2 | 12/2018 | Granada et al. |
| 10,154,906 B2 | 12/2018 | Granada et al. |
| 10,182,908 B2 | 1/2019 | Tubishevitz |
| 10,226,341 B2 | 3/2019 | Gross et al. |
| 10,245,143 B2 | 4/2019 | Gross et al. |
| 10,258,471 B2 | 4/2019 | Lutter et al. |
| 10,321,995 B1 | 6/2019 | Christianson et al. |
| 10,327,895 B2 | 6/2019 | Lozonschi et al. |
| 10,376,361 B2 | 8/2019 | Gross et al. |
| 10,531,872 B2 | 1/2020 | Hacohen et al. |
| 10,548,731 B2 | 2/2020 | Lashinski et al. |
| 2002/0032481 A1 | 3/2002 | Gabbay |
| 2002/0151970 A1 | 10/2002 | Garrison et al. |
| 2004/0186558 A1 | 9/2004 | Pavcnik et al. |
| 2004/0249433 A1 | 12/2004 | Freitag |
| 2005/0137690 A1 | 6/2005 | Salahieh et al. |
| 2005/0240200 A1 | 10/2005 | Bergheim |
| 2005/0251251 A1 | 11/2005 | Cribier |
| 2006/0004469 A1 | 1/2006 | Sokel |
| 2006/0020327 A1 | 1/2006 | Lashinski et al. |
| 2006/0052867 A1 | 3/2006 | Revuelta et al. |
| 2006/0259137 A1 | 11/2006 | Artof et al. |
| 2007/0056346 A1 | 3/2007 | Spenser et al. |
| 2007/0198077 A1 | 8/2007 | Cully et al. |
| 2007/0213810 A1 | 9/2007 | Newhauser et al. |
| 2007/0219630 A1 | 9/2007 | Chu |
| 2008/0071361 A1 | 3/2008 | Tuval et al. |
| 2008/0147182 A1 | 6/2008 | Righini et al. |
| 2008/0200980 A1 | 8/2008 | Robin et al. |
| 2008/0281411 A1 | 11/2008 | Berreklouw |
| 2009/0005863 A1 | 1/2009 | Goetz et al. |
| 2009/0125098 A1 | 5/2009 | Chuter |
| 2009/0157175 A1 | 6/2009 | Benichou |
| 2009/0259306 A1 | 10/2009 | Rowe |
| 2010/0023120 A1 | 1/2010 | Holecek et al. |
| 2010/0100167 A1 | 4/2010 | Bortlein et al. |
| 2010/0161036 A1 | 6/2010 | Pintor et al. |
| 2010/0331971 A1 | 12/2010 | Keranen et al. |
| 2011/0004299 A1 | 1/2011 | Navia et al. |
| 2011/0021985 A1 | 1/2011 | Spargias |
| 2011/0029072 A1 | 2/2011 | Gabbay |
| 2011/0137397 A1 | 6/2011 | Chau et al. |
| 2011/0144742 A1 | 6/2011 | Madrid et al. |
| 2011/0208283 A1 | 8/2011 | Rust |
| 2011/0218620 A1 | 9/2011 | Meiri et al. |
| 2011/0224785 A1 | 9/2011 | Hacohen |
| 2011/0282439 A1 | 11/2011 | Thill et al. |
| 2011/0319989 A1 | 12/2011 | Lane et al. |
| 2012/0016468 A1 | 1/2012 | Robin et al. |
| 2012/0022629 A1 | 1/2012 | Perera et al. |
| 2012/0022639 A1 | 1/2012 | Hacohen et al. |
| 2012/0022640 A1 | 1/2012 | Gross et al. |
| 2012/0059458 A1 | 3/2012 | Buchbinder et al. |
| 2012/0065464 A1 | 3/2012 | Ellis |
| 2012/0078237 A1 | 3/2012 | Wang et al. |
| 2012/0089223 A1 | 4/2012 | Nguyen et al. |
| 2012/0300063 A1* | 11/2012 | Majkrzak ............... A61F 2/2472 348/135 |
| 2012/0310328 A1 | 12/2012 | Olson et al. |
| 2013/0035759 A1 | 2/2013 | Gross et al. |
| 2013/0261738 A1 | 10/2013 | Clague et al. |
| 2014/0000112 A1 | 1/2014 | Braido et al. |
| 2014/0005778 A1 | 1/2014 | Buchbinder et al. |
| 2014/0018915 A1 | 1/2014 | Biadillah et al. |
| 2014/0142688 A1 | 5/2014 | Duffy et al. |
| 2014/0172077 A1 | 6/2014 | Bruchman et al. |
| 2014/0207231 A1 | 7/2014 | Hacohen et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0257467 A1 | 9/2014 | Lane et al. |
| 2014/0277409 A1 | 9/2014 | Börtlein et al. |
| 2014/0277411 A1 | 9/2014 | Börtlein et al. |
| 2014/0277418 A1 | 9/2014 | Miller |
| 2015/0142100 A1 | 5/2015 | Morriss et al. |
| 2015/0157458 A1 | 6/2015 | Thambar et al. |
| 2015/0173896 A1 | 6/2015 | Richter et al. |
| 2015/0173897 A1 | 6/2015 | Raanani et al. |
| 2015/0327994 A1 | 11/2015 | Morriss et al. |
| 2015/0351903 A1 | 12/2015 | Morriss et al. |
| 2015/0351904 A1 | 12/2015 | Cooper et al. |
| 2016/0030169 A1 | 2/2016 | Shahriari |
| 2016/0317305 A1 | 11/2016 | Pelled et al. |
| 2016/0324635 A1 | 11/2016 | Vidlund et al. |
| 2016/0374801 A1 | 12/2016 | Jimenez et al. |
| 2016/0374802 A1 | 12/2016 | Levi et al. |
| 2017/0056166 A1 | 3/2017 | Ratz et al. |
| 2017/0135816 A1 | 5/2017 | Lashinski et al. |
| 2017/0189174 A1 | 7/2017 | Braido et al. |
| 2017/0333187 A1 | 11/2017 | Hariton et al. |
| 2018/0021129 A1 | 1/2018 | Peterson et al. |
| 2018/0206983 A1 | 7/2018 | Noe et al. |
| 2018/0250126 A1 | 9/2018 | O'connor et al. |
| 2018/0296336 A1 | 10/2018 | Cooper et al. |
| 2018/0344457 A1 | 12/2018 | Gross et al. |
| 2018/0353294 A1 | 12/2018 | Calomeni et al. |
| 2019/0053896 A1 | 2/2019 | Adamek-bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0105153 A1 | 4/2019 | Barash et al. |
| 2019/0117391 A1 | 4/2019 | Humair |
| 2019/0175339 A1 | 6/2019 | Vidlund |
| 2019/0183639 A1 | 6/2019 | Moore |
| 2019/0216602 A1 | 7/2019 | Lozonschi |
| 2019/0350701 A1 | 11/2019 | Adamek-bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2020/0000579 A1 | 1/2020 | Manash et al. |
| 2020/0015964 A1 | 1/2020 | Noe et al. |
| 2020/0060818 A1 | 2/2020 | Geist et al. |

FOREIGN PATENT DOCUMENTS

| | | |
|---|---|---|
| WO | 2010006627 A1 | 1/2010 |
| WO | 2010057262 A1 | 5/2010 |
| WO | 2012048035 A2 | 4/2012 |
| WO | 2013/072496 | 5/2013 |
| WO | 2013078497 A1 | 6/2013 |
| WO | 2013175468 A2 | 11/2013 |
| WO | 2014164364 A1 | 10/2014 |
| WO | 2016125160 A1 | 8/2016 |
| WO | 2018029680 A1 | 2/2018 |

(56) References Cited

FOREIGN PATENT DOCUMENTS

WO   2018039631 A1   3/2018
WO   2019/195860   10/2019

OTHER PUBLICATIONS

PCT International Search Report and Written Opinion dated May 13, 2019 in corresponding Application No. PCT/IL2018/051350, 17 pages.
PCT International Search Report and Written Opinion dated Apr. 25, 2019 in corresponding Application No. PCT/IL2019/050142, 12 pages.
PCT International Search Report and Written Opinion dated Jan. 25, 2019 in corresponding Application No. PCT/IL2018/051122, 36 pages.
PCT International Search Report and Written Opinion dated Dec. 5, 2018 in corresponding Application No. PCT/IL2018/050725, 19 pages.
PCT International Preliminary Report on Patentability dated Feb. 12, 2019 in corresponding Application No. PCT/IL2017/050873, 13 pages.
PCT International Preliminary Report on Patentability dated Feb. 5, 2019 in corresponding Application No. PCT/IL2017/050849, 12 pages.
Office Action dated Mar. 25, 2019, issued in European Patent Application No. 14710060.6, 4 pages.
Office Action dated Oct. 25, 2018, issued in U.S. Appl. No. 14/763,004, 18 pages.
Office Action dated Mar. 4, 2019, issued in U.S. Appl. No. 14/763,004, 29 pages.
Office Action dated Jan. 9, 2019, issued in U.S. Appl. No. 15/329,920, 19 pages.
Office Action dated Jan. 30, 2019, issued in U.S. Appl. No. 15/872,501, 34 pages.
Office Action dated Feb. 5, 2019, issued in U.S. Appl. No. 15/899,858, 24 pages.
Office Action dated May 23, 2019, issued in U.S. Appl. No. 15/668,659, 19 pages.
Office Action dated May 1, 2019, issued in U.S. Appl. No. 15/691,032, 113 pages.
Office Action dated May 16, 2019, which issued during the prosecution of U.S. Appl. No. 15/433,547.
Office Action dated Jun. 13, 2019, which issued during the prosecution of U.S. Appl. No. 16/388,038.
Office Action dated Jun. 14, 2019, which issued during the prosecution of U.S. Appl. No. 15/703,385.
Office Action dated Jun. 19, 2019, which issued during the prosecution of U.S. Appl. No. 15/682,789.
Office Action dated Jun. 25, 2019, which issued during the prosecution of U.S. Appl. No. 15/329,920.
Office Action dated Aug. 1, 2019, which issued during the prosecution of U.S. Appl. No. 15/668,559.
Office Action dated Aug. 16, 2019, which issued during the prosecution of U.S. Appl. No. 15/668,659.
Office Action dated Sep. 13, 2019, which issued during the prosecution of U.S. Appl. No. 16/460,313.
Office Action dated Oct. 4, 2019, which issued during the prosecution of U.S. Appl. No. 16/183,140.
Office Action dated Nov. 1, 2019, which issued during the prosecution of U.S. Appl. No. 15/872,501.
Office Action dated Nov. 26, 2019, which issued during the prosecution of U.S. Appl. No. 16/532,945.
An Office Action dated Jan. 6, 2020, which issued during the prosecution of U.S. Appl. No. 16/660,231.
An Office Action dated Dec. 31, 2019, which issued during the prosecution of U.S. Appl. No. 16/183,140.
An Office Action dated Jan. 14, 2020, which issued during the prosecution of U.S. Appl. No. 16/284,331.
Notice of Allowance dated Jan. 13, 2020, which issued during the prosecution of U.S. Appl. No. 15/956,956.
European Search Report dated Mar. 5, 2020 which issued during the prosecution of Applicant's European App No. 17752184.6.
European Search Report dated Mar. 4, 2020 which issued during the prosecution of Applicant's European App No. 16706913.7.
Notice of Allowance dated Mar. 12, 2020, which issued during the prosecution of U.S. Appl. No. 16/460,313.
An Office Action dated Jan. 9, 2020, which issued during the prosecution of U.S. Appl. No. 15/600,190.
An Office Action dated Jan. 3, 2020, which issued during the prosecution of U.S. Appl. No. 16/678,355.
An Office Action dated Feb. 6, 2020, which issued during the prosecution of U.S. Appl. No. 15/668,659.
Notice of Allowance dated Dec. 22. 2017, which issued during the prosecution of U.S. Appl. No. 15/788,407.
An international Search Report and a Written Opinion both dated Jun. 20. 2018, which issued during the prosecution of Applicant's PCT/IL20I8/050024.

* cited by examiner

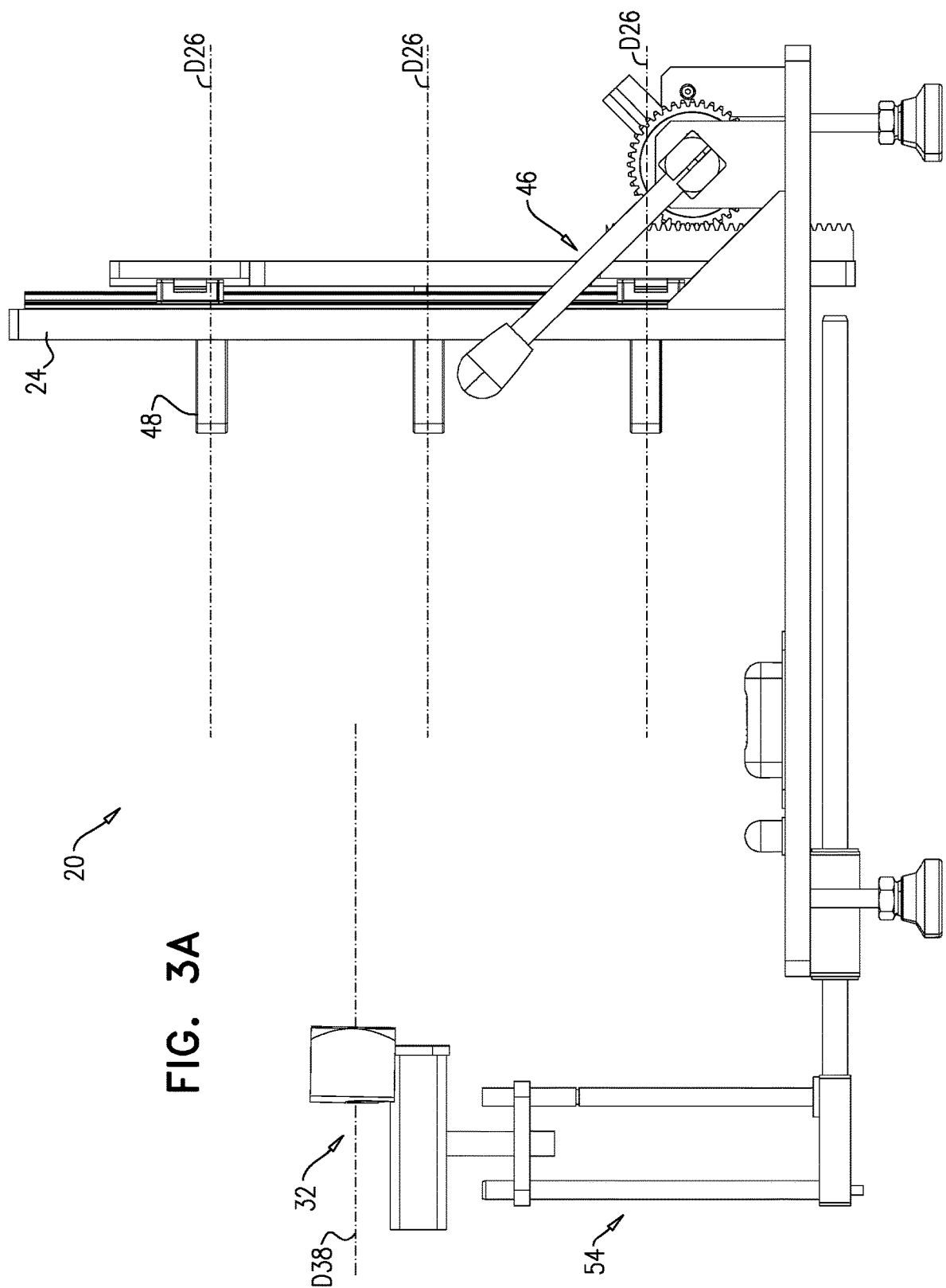

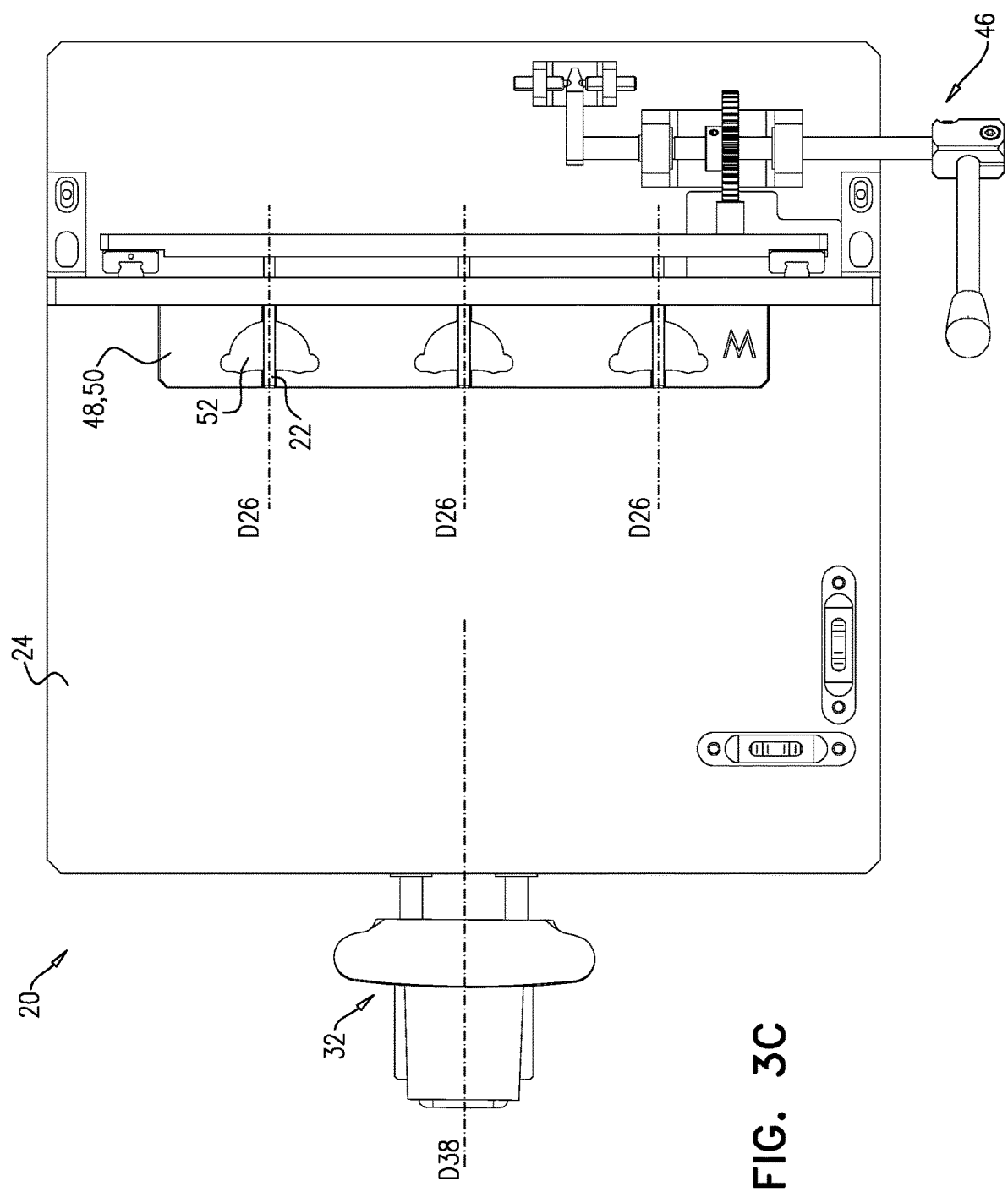

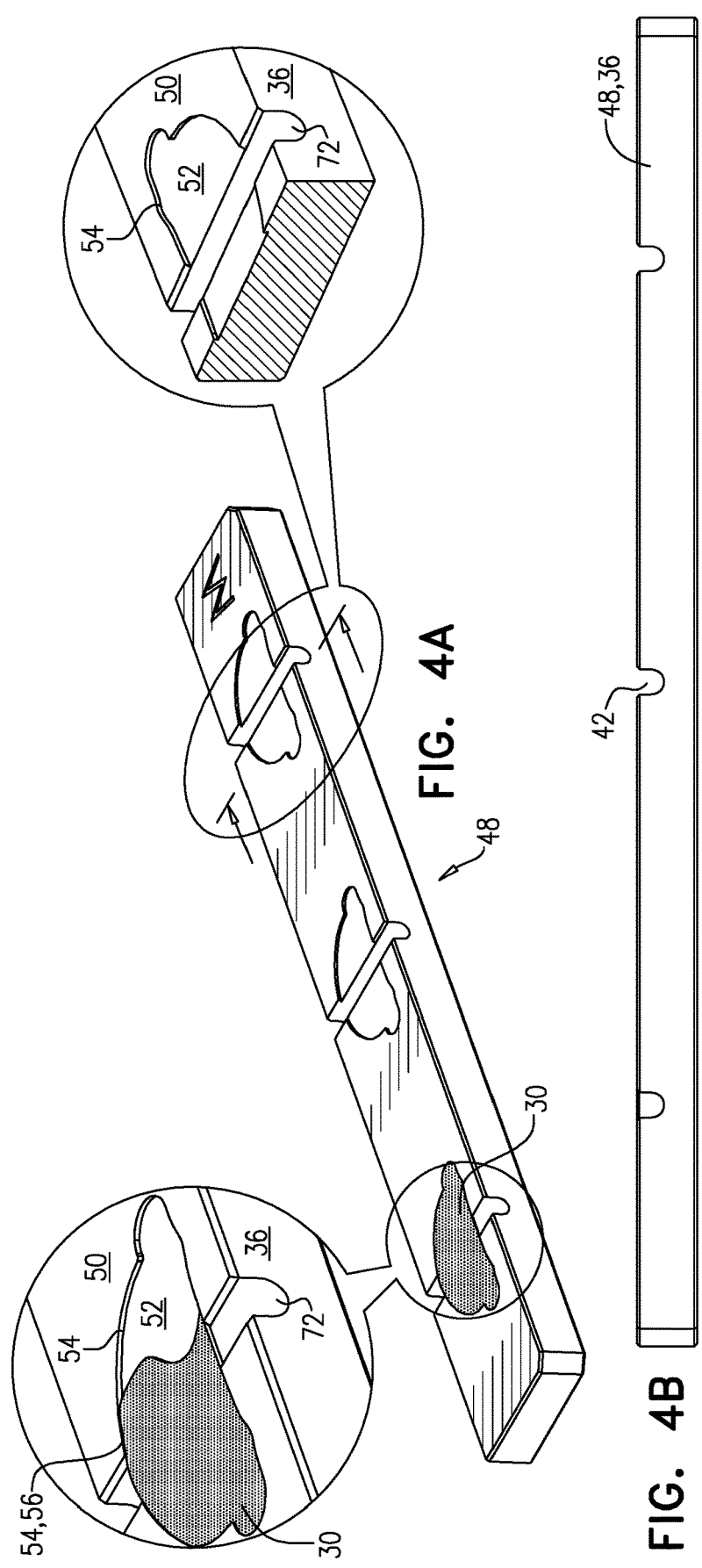

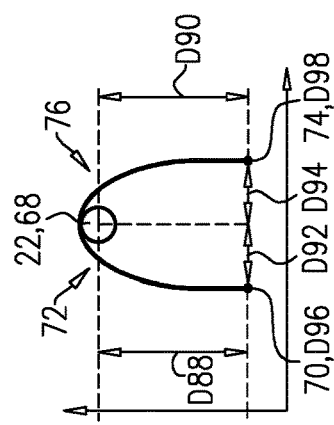
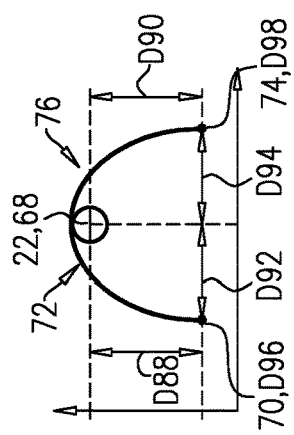
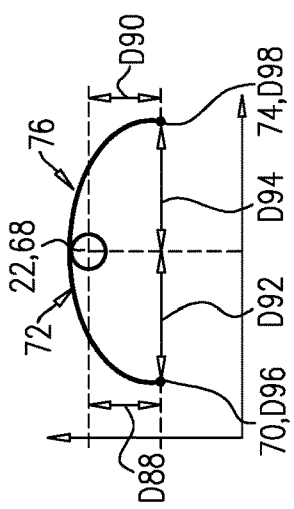
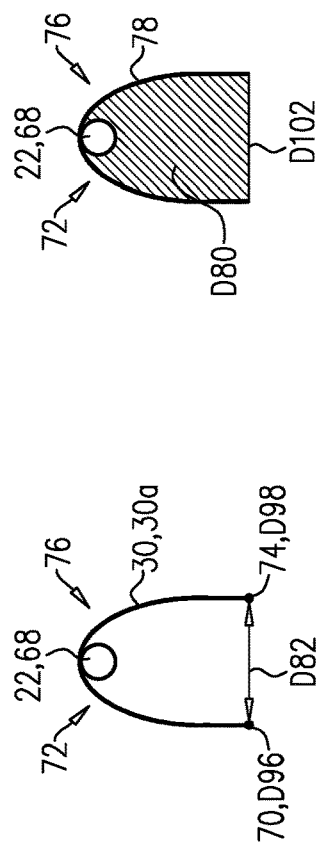
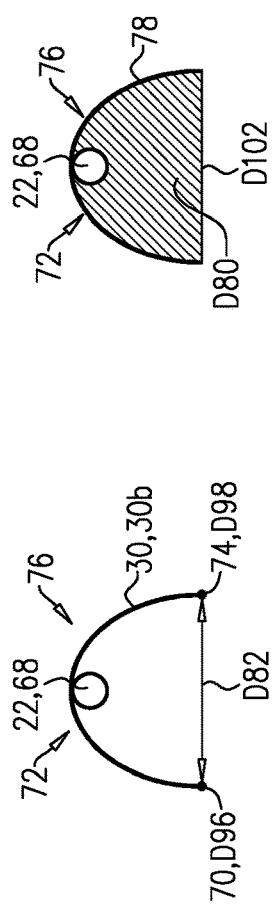
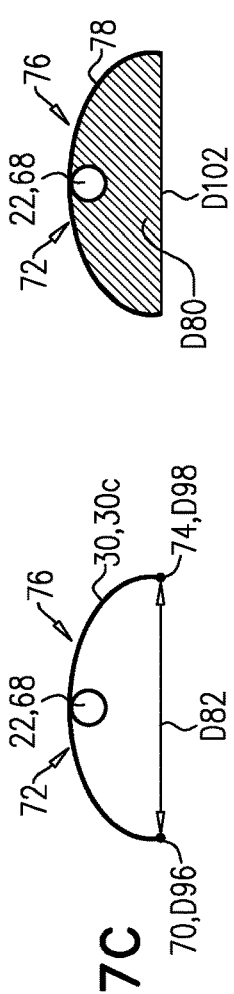
FIG. 7A
FIG. 7B
FIG. 7C

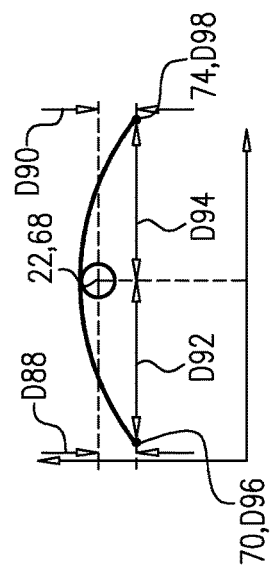
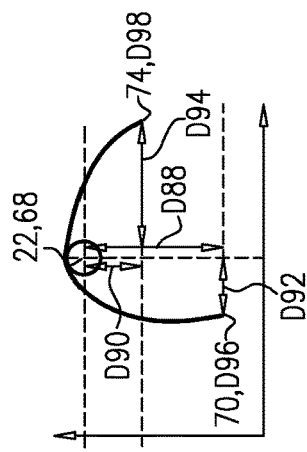
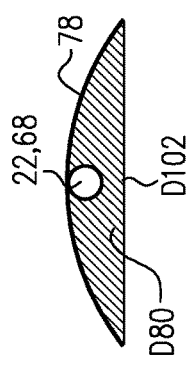
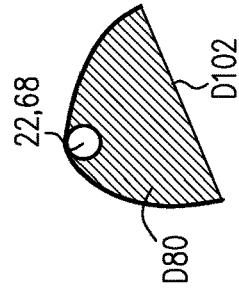
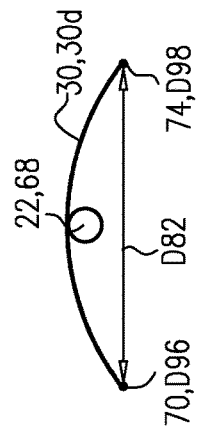
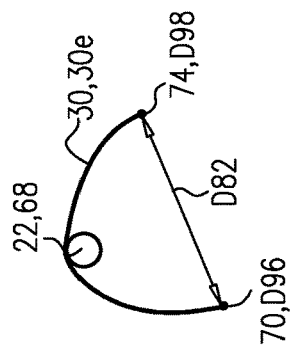
FIG. 8A
FIG. 8B

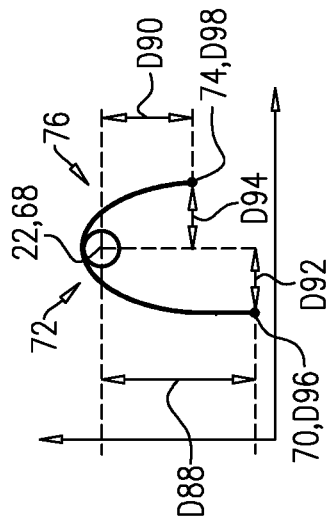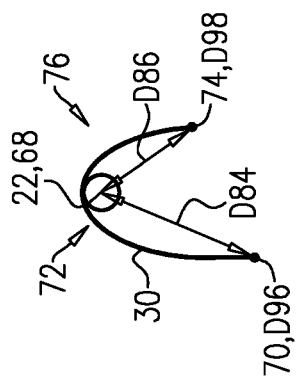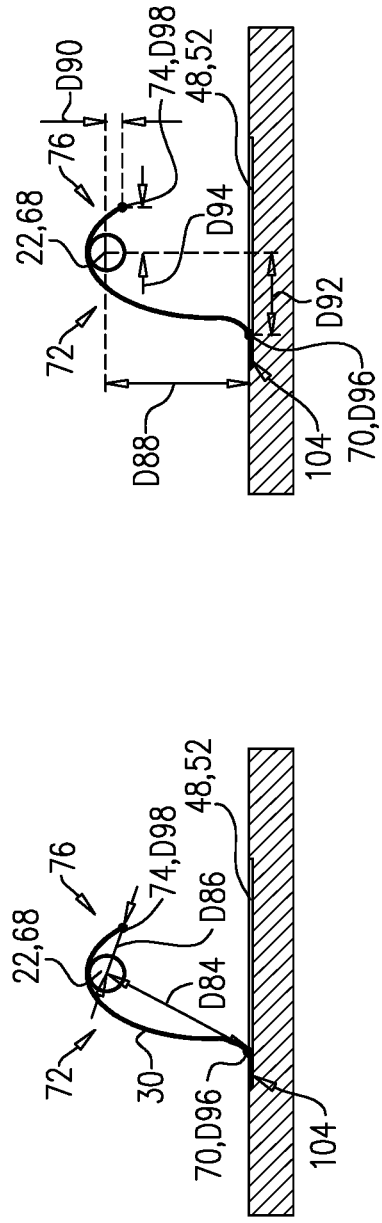
FIG. 9A
FIG. 9B

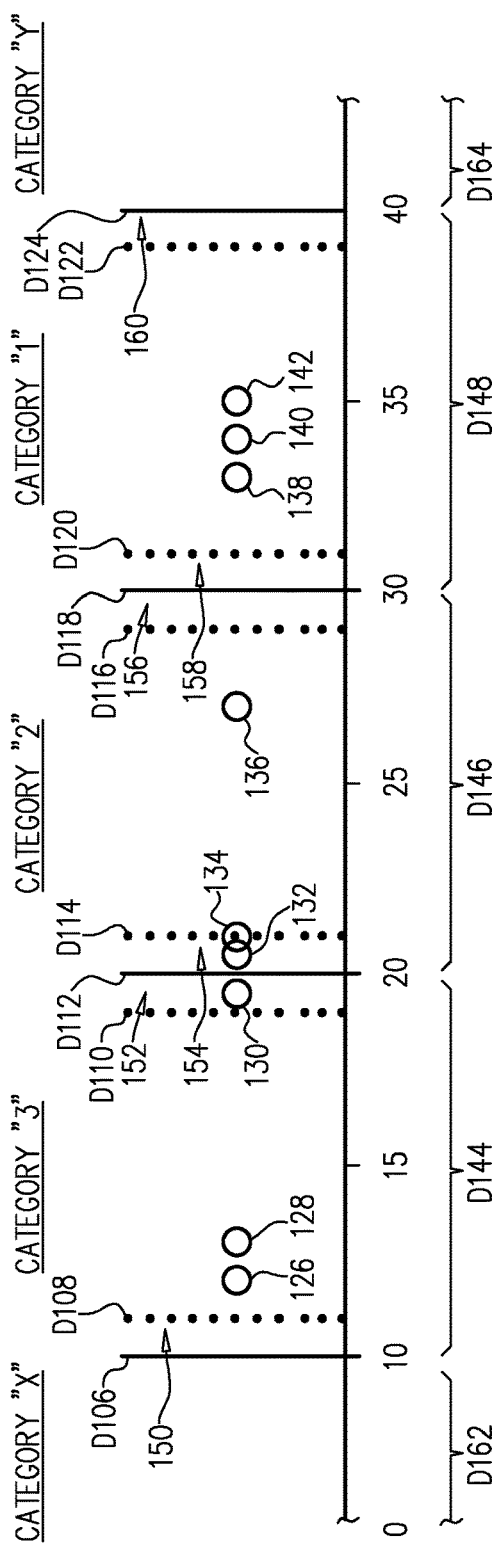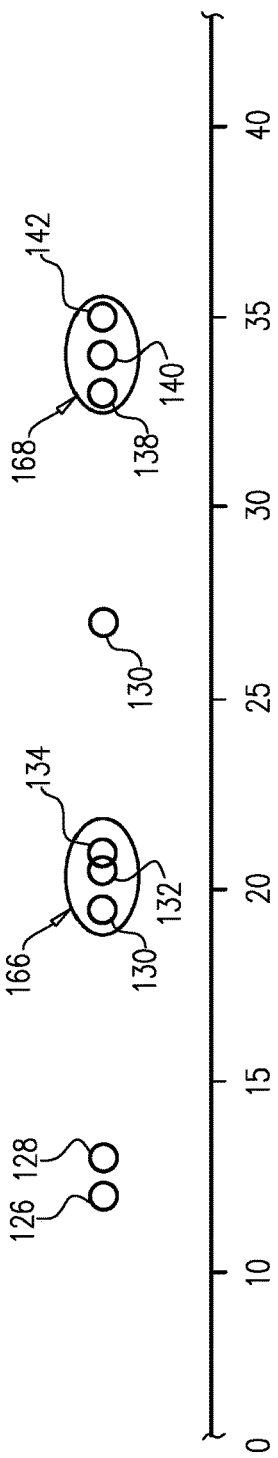
FIG. 11A
FIG. 11B

LEAFLET-TESTING APPARATUS

FIELD OF THE INVENTION

Some applications of the present invention relate in general to prosthetic heart valves. More specifically, some applications of the present invention relate to techniques for testing the flexibility of prosthetic leaflets to be used in prosthetic heart valves.

BACKGROUND

Prosthetic heart valves may be constructed of a frame to which prosthetic leaflets are attached, the leaflets providing check-valve functionality by opening in response to blood flow in a first direction, and closing in response to blood flow in a second direction. In order to inhibit leakage ("regurgitation") of blood between the closed leaflets in the second direction, it is important that the leaflets coapt well against each other. One factor facilitating coaptation of leaflets in a prosthetic heart valve is flexibility of leaflets.

SUMMARY OF THE INVENTION

Some applications of the present invention are directed to determining flexibility of prosthetic heart valve leaflets. Sorting leaflets into groups or categories of similarly flexible leaflets (e.g., to be sewn together in a prosthetic heart valve) may facilitate the preparation of properly functioning prosthetic heart valves.

Aspects of the present invention include apparatus and methods for computationally assigning values indicative of leaflet flexibility to leaflets, by digital analysis of an image including a plurality of leaflets draped over a plurality of bars.

Some aspects of the present invention include sorting the leaflets into leaflet categories, each leaflet category being characterized by the at least one value indicative of leaflet flexibility.

Other aspects of the present invention include grouping leaflets into groups in response to similarity, for each leaflet grouped into a group, of at least one value indicative of leaflet flexibility.

There is therefore provided, in accordance with an application of the present invention, apparatus for testing a plurality of prosthetic heart valve leaflets, the apparatus including:

a vertical mount;

a plurality of horizontal bars movably coupled to the mount, each bar extending away from the mount along a respective bar-axis that lies on a respective vertical bar-plane, and each bar configured to support a respective leaflet along the respective bar-axis such that the respective leaflet drapes over the respective bar; and an image sensor, positioned opposite the mount, facing the plurality of bars and the mount so as to be oriented to acquire an image that includes the plurality of leaflets draped over the plurality of bars.

In an application, the mount is generally flat, and the plurality of horizontal bars are generally parallel with each other.

In an application, the mount is concave toward the image sensor.

In an application, the apparatus includes exactly one image sensor.

In an application, the apparatus includes an image output device configured to transmit the image.

In an application, the apparatus includes a sensor-bracket that movably couples the image sensor to the mount, such that the image sensor is movable along a sensor-axis with respect to the mount.

In an application, the apparatus includes circuitry, configured to receive the image, and to analyze the image, the analysis of the image being such that, for each of the leaflets included in the image, the circuitry derives a corresponding flexibility value that is indicative of flexibility of the leaflet.

In an application, the circuitry is configured to, for each of the leaflets, identify a draping-contour line, and to derive the value at least in part responsively to an Area Under Curve value defined by the draping-contour line.

In an application, the circuitry is configured to assign a respective flexibility category to each of the leaflets, responsively to the flexibility value.

In an application, the apparatus includes at least one indicator that is in communication with the circuitry, the indicator configured to indicate the respective category assigned to each leaflet.

In an application, the apparatus includes a respective indicator for each of the leaflets, each of the indicators being configured to indicate the respective category assigned to the respective leaflet.

In an application, each of the indicators is disposed adjacent to the respective bar that supports the respective leaflet.

In an application, the circuitry is configured:

with a plurality of flexibility categories, each flexibility category having an upper flexibility-value threshold and a lower flexibility-value threshold, to assign a respective flexibility category to each leaflet, responsively to the flexibility value of the leaflet falling between the upper flexibility-value threshold and the lower flexibility-value threshold for the category, and for a leaflet that has a flexibility value that falls within a margin of a threshold value, to indicate a recommendation that the leaflet be manually assigned to a flexibility category.

In an application:

each of the bars extends away from the mount towards a respective bar-tip, and each of the bars is configured to support a respective leaflet along the respective bar-axis such that the respective leaflet drapes over the respective bar such that a first-leaflet-tip is disposed below the bar on a first side of the bar, and a second-leaflet-tip is disposed below the bar on a second side of the bar.

In an application, the circuitry is configured to identify the first-leaflet-tip and the second-leaflet tip, and to derive the value at least in part responsively to a first-leaflet-tip position of the first leaflet tip and a second-leaflet-tip position of the second leaflet tip.

In an application, the circuitry is configured to derive the value at least in part responsively to a vertical height of the first-leaflet-tip position and a vertical height of the second-leaflet-tip position.

In an application, the circuitry is configured to derive the value at least in part responsively to a horizontal location of the first-leaflet-tip position and a horizontal location of the second-leaflet-tip position.

In an application, the circuitry is configured to derive the value at least in part responsively to:

a direct distance between the first-leaflet-tip position and a bar-tip of the respective bar, and a direct distance between the second-leaflet-tip position and the bar-tip of the respective bar.

In an application, the circuitry is configured to derive the value at least in part responsively to a direct distance between the first-leaflet-tip position and the second-leaflet-tip position.

In an application, the circuitry is configured to group the leaflets into groups, based on similarity between (i) the flexibility value of each leaflet of the plurality of leaflets, and (ii) the respective flexibility value of other leaflets of the plurality of leaflets, each of the groups including a predetermined number of leaflets.

In an application, the predetermined number of leaflets in each group is two leaflets.

In an application, the predetermined number of leaflets in each group is three leaflets.

In an application, the apparatus includes at least one indicator that is in communication with the circuitry, the indicator configured to indicate the respective group to which each leaflet is grouped.

In an application, the apparatus includes a respective indicator for each of the leaflets, each of the indicators being configured to indicate the respective group to which each leaflet is grouped.

In an application, each of the indicators is disposed adjacent to the respective bar that supports the respective leaflet.

In an application, the apparatus includes:
a platform having an upper surface, the platform coupled to the mount such that the bar-plane intersects the platform; and
an actuator, actuation of the actuator moving the bar vertically, in the bar-plane, with respect to the platform.

In an application, the bar has an initial position with respect to the platform, in which the leaflet is placeable across the bar such that the leaflet is in contact with the surface.

In an application, in the initial position, the bar is disposed below the surface.

In an application, the platform has a guide that defines a guide-outline that corresponds to a leaflet-outline of the leaflet, such that when the leaflet is placed on the surface with the leaflet-outline aligned with the guide-outline, the leaflet is disposed across the bar.

In an application, the platform is disposed with respect to the bar such that the bar-plane bisects the guide-outline.

In an application, the platform is disposed with respect to the bar such that the bar-plane bisects the guide-outline symmetrically.

In an application, the surface of the guide is at least partially included of a low-friction material.

In an application, the low-friction material is Teflon.

In an application, the bars extend away from the mount in parallel with each other.

In an application, the bars are arranged, with respect to the mount, in multiple rows and multiple columns.

In an application, the mount is a strong color.

In an application, the apparatus includes:
a platform having an upper surface, the platform coupled to the mount such that the bar-plane intersects the platform; and
an actuator, actuation of the actuator moving the bar vertically, in the bar-plane, with respect to the platform, and:
the strong color of the mount is a first strong color, and the platform is a second strong color that is distinct from the first strong color.

In an application:
the strong color of the mount is a first strong color, and
each of the bars has an end, at least the end of the bar being a second strong color that is distinct from the first strong color.

There is further provided, in accordance with an application of the present invention, a system for testing a plurality of prosthetic heart valve leaflets, the system including:
a tester, the tester including:
a vertical mount;
a plurality of horizontal bars movably coupled to the mount, each bar extending away from the mount along a respective bar-axis that lies on a respective vertical bar-plane, and each bar configured to support a respective leaflet along the respective bar-axis such that the respective leaflet drapes over the respective bar; and an image sensor, positioned opposite the mount, facing the plurality of bars and the mount so as to be oriented to acquire an image that includes the plurality of leaflets draped over the plurality of bars; and
software, the software configured to receive the image, and to analyze the image such that, for each of the leaflets included in the image, the circuitry derives a corresponding flexibility value that is indicative of flexibility of the leaflet.

In an application, the apparatus includes circuitry, configured to run the software.

In an application, the circuitry is coupled to the tester.

There is further provided, in accordance with an application of the present invention, a method for determining flexibility of prosthetic heart valve leaflets, the method including:
placing each prosthetic heart valve leaflet of a plurality of prosthetic heart valve leaflets across a respective bar of a plurality of bars, each of the bars:
being movably coupled to a vertical mount, and
extending horizontally away from the mount;
lifting each bar of the plurality of bars vertically in a respective vertical bar-plane such that each of the bars supports the respective leaflet, and the respective leaflet drapes over the respective bar; and
obtaining, for each respective leaflet, a leaflet-flexibility categorization, the leaflet-flexibility categorization being computationally assigned to the leaflet responsively to a value indicative of leaflet flexibility, the value being derived by digital analysis of an image that includes the plurality of leaflets draped over the plurality of bars.

There is further provided, in accordance with an application of the present invention, a method for determining flexibility of prosthetic heart valve leaflets, the method including:
placing each prosthetic heart valve leaflet of a plurality of prosthetic heart valve leaflets across a respective bar of a plurality of bars such that:
each of the bars supports a respective leaflet, and
the respective leaflet drapes over the respective bar, each of the bars:
being coupled to a vertical mount, and
extending horizontally away from the mount, and
obtaining, for each respective leaflet, at least one value indicative of leaflet flexibility, the at least one value being derived by digital analysis of an image that includes the plurality of leaflets draped over the plurality of bars; and
sorting the leaflets into leaflet categories, each leaflet category being characterized by the at least one value indicative of leaflet flexibility.

In an application, obtaining includes activating an image sensor, the image sensor:
  positioned opposite the mount,
  facing the plurality of bars and the mount; and
  oriented to acquire an image that includes the plurality of leaflets draped over the plurality of bars.

In an application, obtaining further includes activating circuitry to perform the digital analysis.

In an application, the method includes, prior to activating the circuitry to perform the digital analysis, activating the circuitry to perform a calibration routine.

In an application, activating the circuitry to perform the digital analysis includes activating the circuitry to analyze a calibration image that includes the plurality of bars.

In an application, the method includes adjusting a position of the image sensor with respect to the plurality of bars.

In an application, adjusting the position of the image sensor includes adjusting a field of view of the image sensor.

There is further provided, in accordance with an application of the present invention, a method, including:
  using an image sensor, acquiring a digital image that includes a plurality of prosthetic heart valve leaflets, each leaflet draped across a respective bar of a plurality of bars;
  using circuitry:
  receiving the image,
  calculating one or more image parameters for each leaflet by digitally analyzing the image;
  deriving, for each leaflet, a leaflet-flexibility value in response to the one or more image parameters for the corresponding leaflet; and
  assigning, to each leaflet, a leaflet-flexibility category in response to the leaflet-flexibility value of the corresponding leaflet; and
  indicating, on at least one indicator, the leaflet-flexibility category of each leaflet.

In an application, calculating includes identifying a draping-contour line, and calculating an area under a curve defined by the draping-contour line.

In an application, the method includes, prior to calculating the one or more image parameters for each leaflet, performing a calibration routine by analyzing a calibration image that includes the plurality of bars.

In an application, calculating includes identifying the location of a first-leaflet-tip and a second-leaflet-tip.

In an application, calculating includes identifying a vertical height of the first-leaflet-tip, and a vertical height of the second-leaflet-tip.

In an application, calculating includes identifying a horizontal location of the first-leaflet-tip, and a horizontal location of the second-leaflet-tip.

In an application, calculating includes identifying a direct distance between the first-leaflet-tip and the second-leaflet-tip.

In an application, calculating further includes identifying the location of a bar-tip disposed at an end of the bar over which the leaflet is draped.

In an application, calculating includes calculating:
  a direct distance between the first-leaflet-tip and the bar-tip of the bar over which the leaflet is draped, and
  a direct distance between the second-leaflet-tip and the bar-tip of the bar over which the leaflet is draped.

In an application, calculating includes calculating:
  a length of a leaflet draping-contour line between the bar-tip and the first-leaflet-tip, and
  a length of a leaflet draping-contour line between the bar-tip and the second-leaflet-tip.

There is further provided, in accordance with an application of the present invention, a method for use with a plurality of prosthetic heart valve leaflets, the method including:
  placing each prosthetic heart valve leaflet of the plurality of prosthetic heart valve leaflets across a respective bar of a plurality of bars such that:
    each of the bars supports a respective leaflet, and
    the respective leaflet drapes over the respective bar, each of the bars:
      being coupled to a vertical mount, and
      extending horizontally away from the mount, and
    obtaining, for each respective leaflet, a grouping into one of a plurality of groups, the grouping being responsive to similarity between (i) a flexibility value of each leaflet of the plurality of leaflets, and (ii) a respective flexibility value of other leaflets of the plurality of leaflets, the flexibility values being derived by digital analysis of an image that includes the plurality of leaflets draped over the plurality of bars; and
    sorting the leaflets into groups, responsively to the obtained grouping.

In an application, obtaining includes activating an image sensor, the image sensor:
  positioned opposite the mount,
  facing the plurality of bars and the mount; and
  oriented to acquire an image that includes the plurality of leaflets draped over the plurality of bars.

In an application, obtaining further includes activating circuitry to perform the digital analysis.

In an application, the method includes, prior to activating the circuitry to perform the digital analysis, activating the circuitry to perform a calibration routine.

In an application, activating the circuitry to perform the digital analysis includes activating the circuitry to analyze a calibration image that includes the plurality of bars.

In an application, the method includes adjusting a position of the image sensor with respect to the plurality of bars.

In an application, adjusting the position of the image sensor includes adjusting a field of view of the image sensor.

The present invention will be more fully understood from the following detailed description of applications thereof, taken together with the drawings, in which:

BRIEF DESCRIPTION OF THE DRAWINGS

FIGS. 3A-C are schematic illustrations of side, front, and top views, respectively, of the tester in the first state, in accordance with some applications of the invention;

FIGS. 4A-C are schematic illustrations showing an arrangement of a platform having a plurality of guides, with respect to a leaflet, in accordance with some applications of the invention;

FIGS. 7A-C are schematic illustrations showing image parameters that may be calculated by circuitry in order to derive a flexibility value, in accordance with some applications of the invention;

FIGS. 8A-B are schematic illustrations of unsuitable leaflets, in accordance with some applications of the invention;

FIGS. 9A-B are schematic illustrations of leaflets whose image parameters and/or leaflet-flexibility values may not enable circuitry to accurately assign leaflets to a leaflet flexibility category, in accordance with some applications of the invention;

FIGS. 11A-B are graphs representing relationships between leaflet-flexibility values of a set of leaflets, and the leaflet-flexibility categories or groups to which the same leaflets are assigned, in accordance with some applications of the invention.

DETAILED DESCRIPTION OF EMBODIMENTS

Figure 1A:
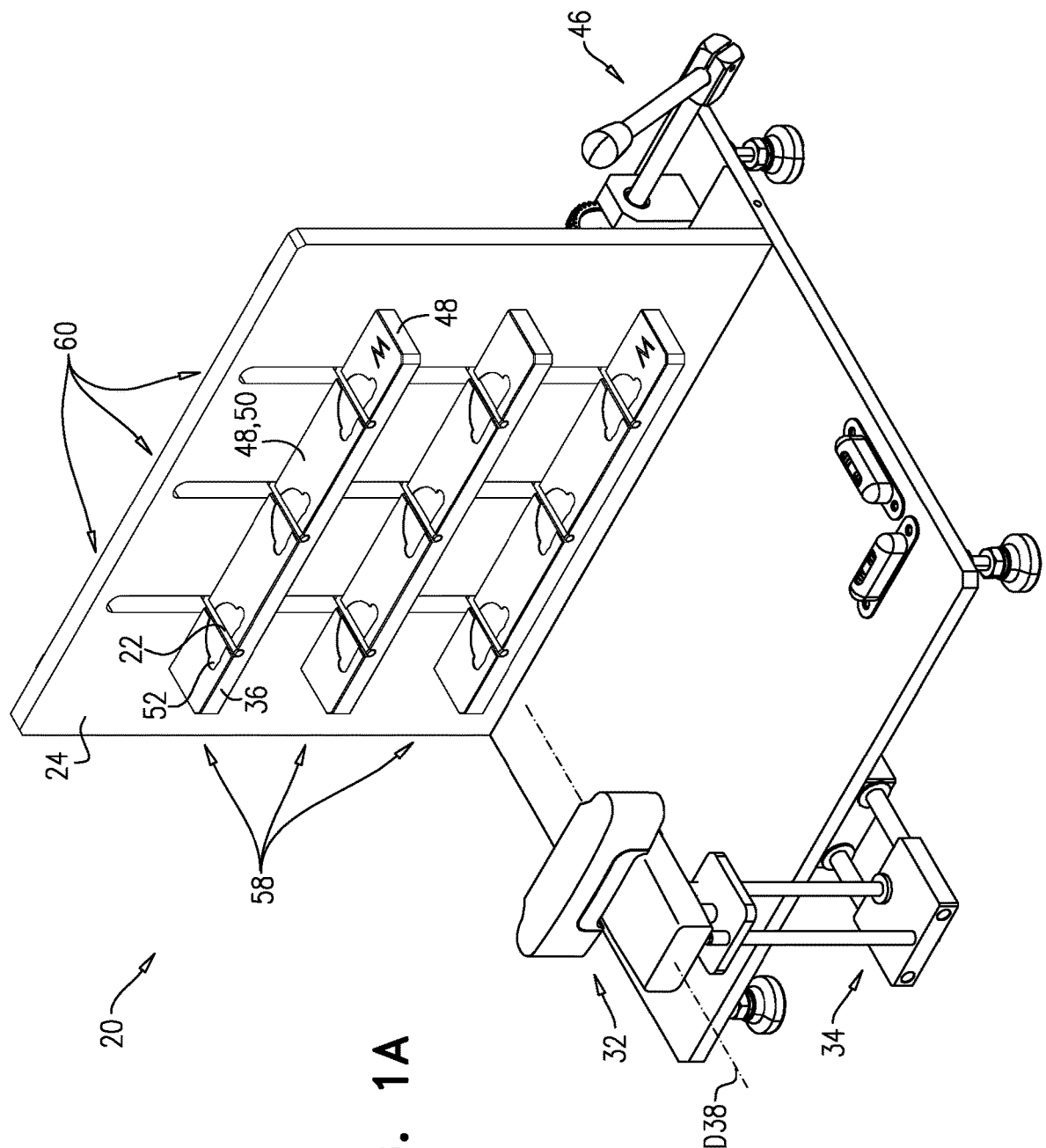
FIGS. 1A-B are schematic illustrations of a tester for testing flexibility of a plurality of prosthetic heart valve leaflets, in a first state and an elevated state, respectively, in accordance with some applications of the invention.
Figure 1B:
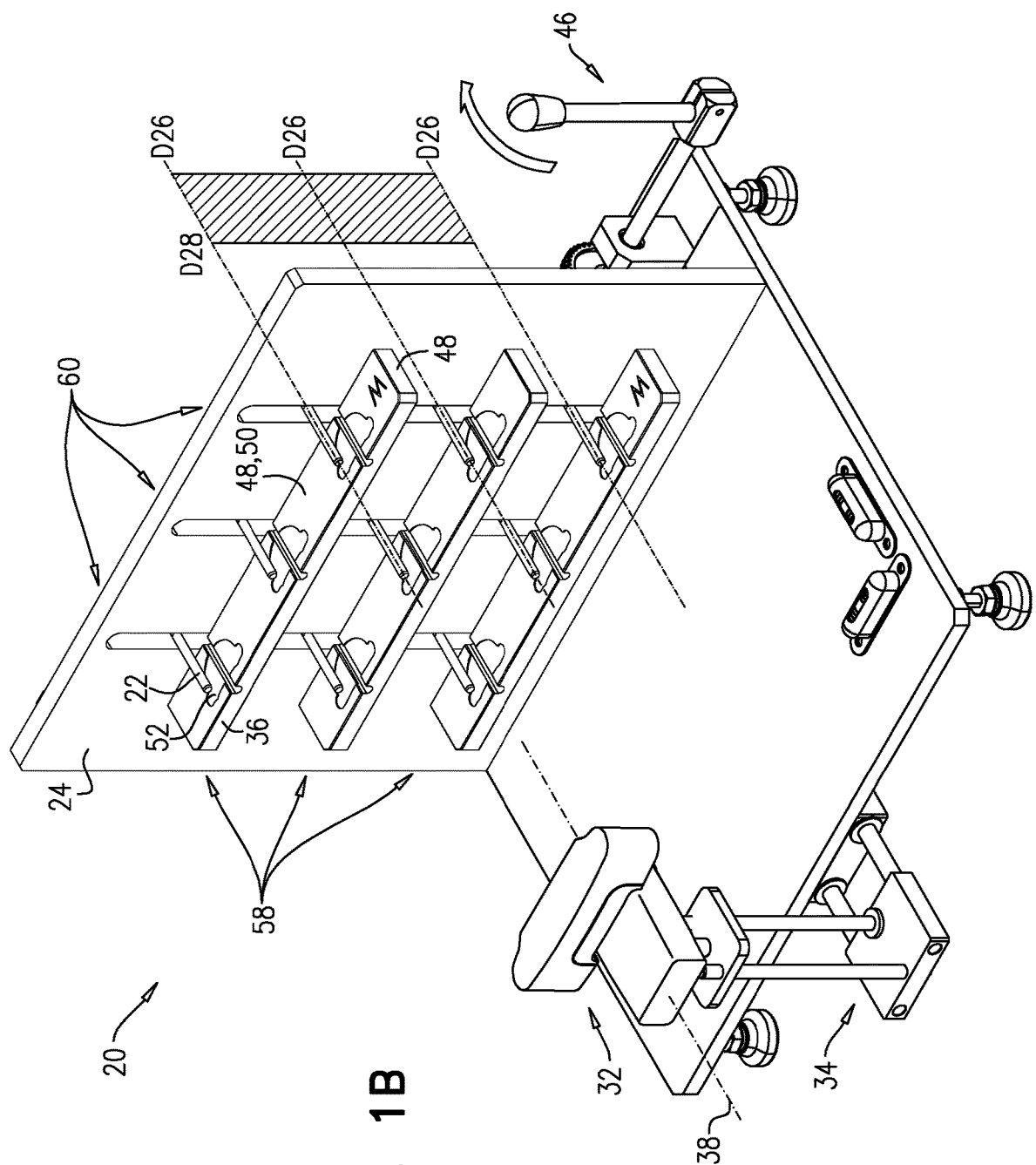
Figure 2:
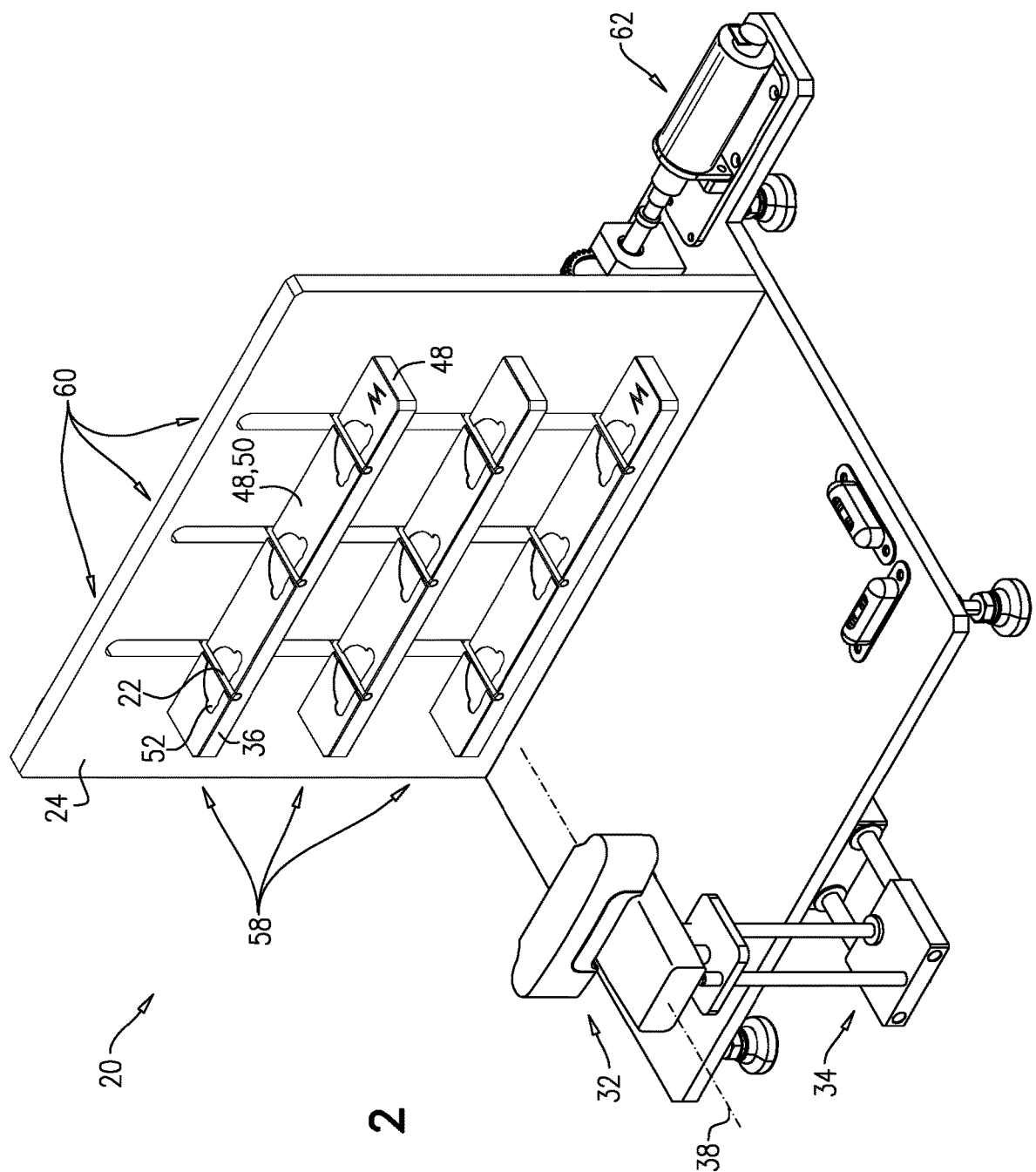
FIG. 2 is a schematic illustration of an alternative embodiment of the tester, in accordance with some applications of the invention.
Figure 3B:
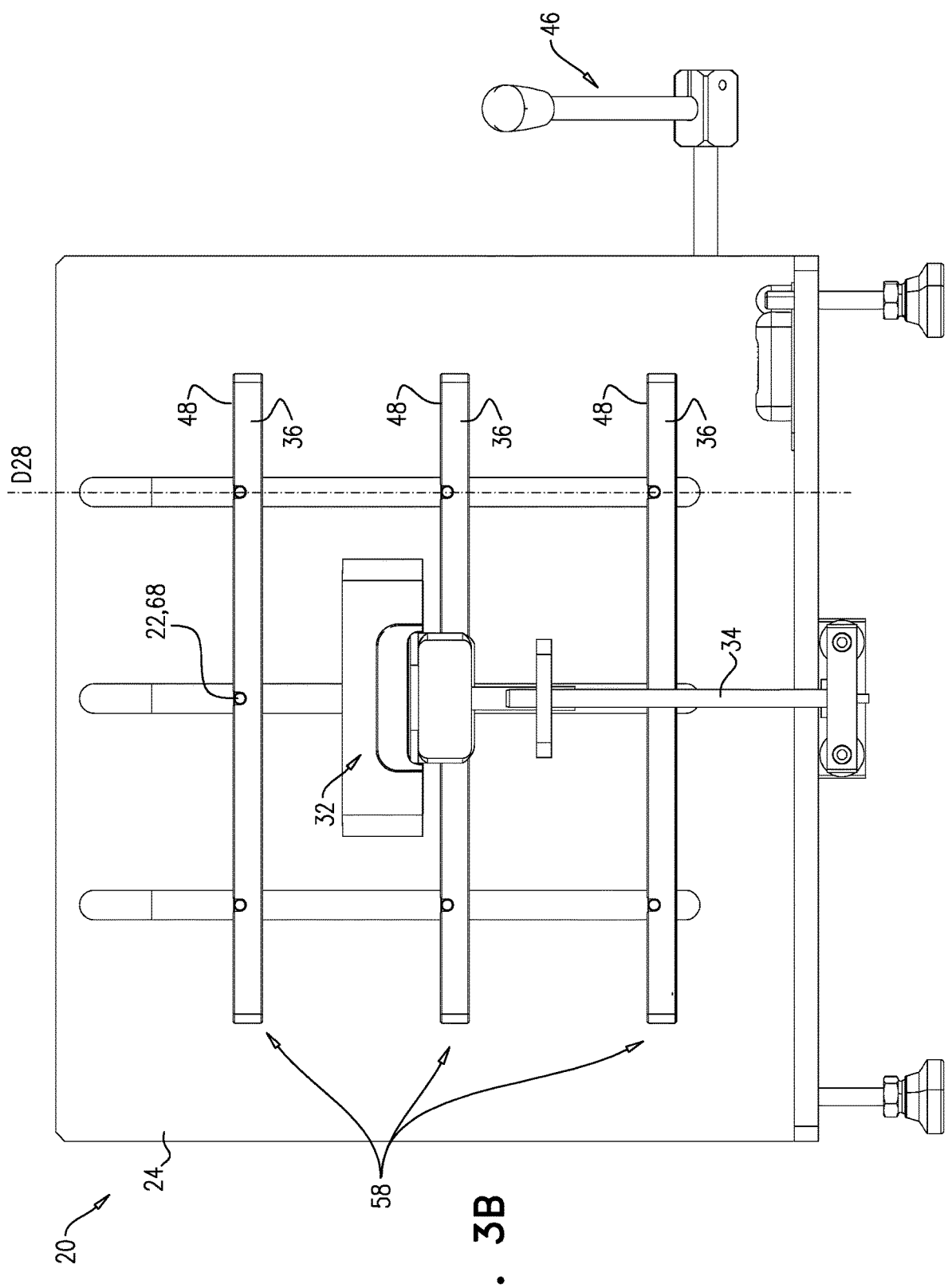

Reference is made to FIGS. 1A-B, 2, and 3A-C, which are schematic illustrations showing a tester 20 for testing flexibility of a plurality of prosthetic heart valve leaflets, in accordance with some applications of the invention. FIGS. 1A-B are perspective views of tester 20 in a first state and an elevated state, respectively. FIG. 2 is a perspective view of an alternative embodiment of tester 20. FIGS. 3A-C are side, front, and top views, respectively, of tester 20 in the first state.

Tester 20 comprises a plurality of horizontal bars 22 movably coupled to a vertical mount 24, in accordance with some applications of the invention. Typically, and as shown, each bar 22 extends away from mount 24 (e.g., perpendicularly from the mount) along a respective bar-axis D26, each bar-axis lying on a respective vertical bar-plane D28.

Tester 20 has a first state (FIGS. 1A, 3A-C) and an elevated state (FIG. 1B). For some applications, and as shown, bars 22 are cylindrically shaped. For other applications, bars 22 may be of an alternate shape (e.g., rectangular prism, hexagonal prism or octagonal prism). Typically, actuation of an actuator 46 reversibly transitions tester 20 between the first state and the elevated state. Actuator 46 is shown as a manually-operated (e.g., mechanical) actuator. For some applications (FIG. 2), an electrical (e.g., motorized) actuator 62 may be used instead.

As shown in FIGS. 1A-B, transitioning of tester 20 between the first and elevated states includes vertical motion of each bars 22 along its vertical bar-plane D28 with respect to a platform 48. Typically, actuator 46 moves bars 22 upward with respect to the rest of tester 20, and platform 48 remains stationary. However, the scope of the invention includes actuator 46 moving platform 48 downward with respect to the rest of tester 20, while bars 22 remain stationary. Typically, and as shown, the platform is coupled to mount 24 such that each bar-plane D28 intersects the platform.

Tester 20 further comprises an image sensor 32, the image sensor positioned opposite mount 24, facing bars 22 and the mount. Orientation of image sensor 32 facing mount 24 and bars 22 facilitates the image sensor acquiring an image that includes leaflets 30 (e.g., all of the leaflets) draped over bars 22. Typically, and as shown, tester 20 further comprises a sensor-bracket 34, the sensor-bracket movably coupling image sensor 32 to the rest of tester 20 (e.g., to mount 24).

Typically, sensor-bracket facilitates movement of image sensor 32 along a sensor-axis D38, moving the image sensor toward and away from mount 24. Sensor-bracket 34 typically facilitates movement of image sensor 32 (e.g., along sensor-axis D38) between (i) a position in which the image sensor can acquire an image that includes all of leaflets 30, and (ii) a position in which tester 20 is more compact—e.g., for when the tester is not in use. Typically, tester 20 is operated such that sensor 32 acquires an image that includes the multiple leaflets draped over bars 22. It is hypothesized by the inventors that acquiring and processing an image that includes multiple leaflets increases work throughput and/or improves accuracy of leaflet flexibility testing.

Typically, and as shown, mount 24 is generally flat, and bars 22 are generally parallel with each other. For some applications, mount 24 may be concave toward sensor 32, and bar-tips are arranged correspondingly to the concave surface of the mount, e.g., pointing toward the sensor. It is hypothesized by the inventors that, for some applications, mount 24 being concave may facilitate visualization of all leaflets 30 and bar-tips 68, from a single point of view—i.e., by sensor 32.

Some embodiments of the invention may comprise a plurality of image sensors 32. For example, the number of image sensors 32 may correspond to the number of bars 22.

Reference is made to FIGS. 4A-5A, which are schematic illustrations showing the arrangement of platform 48 with respect to bars 22 and mount 24, in accordance with some applications of the invention. Typically, and as shown, bars 22 extend away from mount 24 in parallel with each other. For some applications, and as shown, bars 22 are arranged, with respect to the mount, in multiple rows 58 and multiple columns 60. For some applications in which bars 22 are arranged in multiple rows (i.e., such that bars 22 are stacked in at least one column), bars 22 may be arranged with respect to mount 24 such that the bar-planes D28 of the bars in a given column are coplanar—i.e., are disposed in a common bar-plane D28—as shown. Although the Figures referred to herein depict an embodiment of tester 20 with bars 22 arranged in three rows 58 and three columns 60, this depiction is not intended to exclude other possible arrangements with either a smaller or greater number of rows 58 or columns 60 of bars 22. For some applications, and as shown, nine bars 22 may be arranged in rows 58 and columns 60 such that image sensor 32 may acquire an image including nine leaflets 30, each leaflet draped over a respective bar. For other applications, tester 20 may comprise a greater or lesser number of bars 22 arranged with respect to mount 24, mutatis mutandis. For some applications, the number of bars 22 is a multiple of 3, e.g., such that all of the leaflets being tested in a single batch may be divided into groups of 3 matching leaflets, each group being used in a respective tri-leaflet prosthetic valve.

Typically, and as shown, platform 48 has an upper surface 50, the upper surface including a guide 52 that defines a guide-outline 54 corresponding to a leaflet-outline 56 of leaflet 30. In some applications, upper surface 50 at guide 52 may comprise a low-friction material. For example, the low-friction material may comprise polytetrafluoroethylene (e.g., Teflon™). Alternatively or additionally, the texture of upper surface 50 may be modified at guide 52. For example, the texture of upper surface 50 may be made to be more smooth (e.g., polished) at guide 52. The use of low-friction material and/or texture for upper surface 50 of guide 52 is hypothesized by the inventors to facilitate release of leaflet 30 from the surface as bar 22 lifts the leaflet away from the surface, thereby facilitating use of tester 20.

Figure 5A:
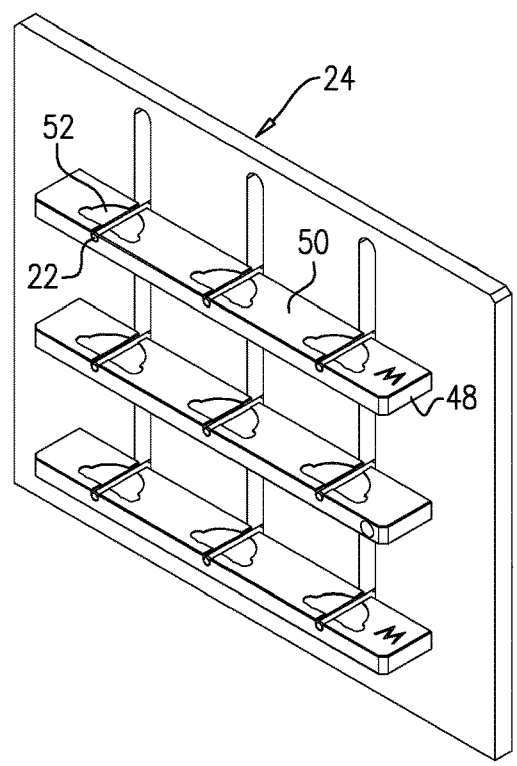
FIGS. 5A-C are schematic illustrations showing the arrangement of platforms with respect to bars and a mount, showing lifting of bars such that each bar supports a leaflet, with the leaflet draped over the bar, in accordance with some applications of the invention.
Figure 5B:
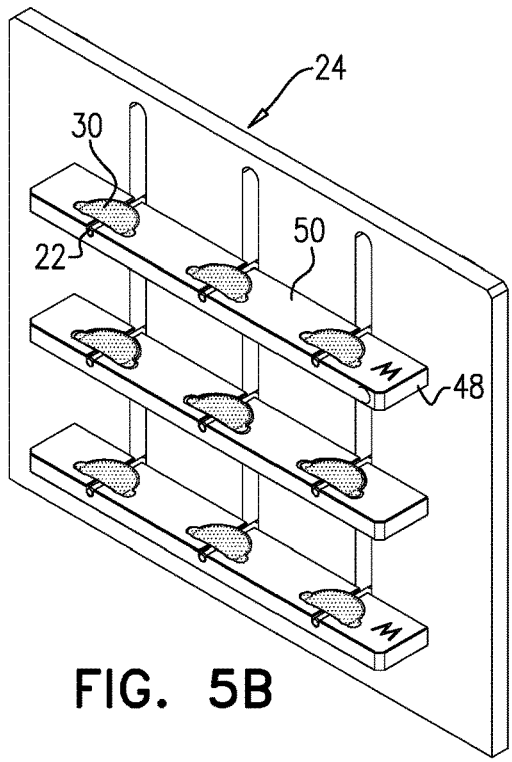
Figure 5C:
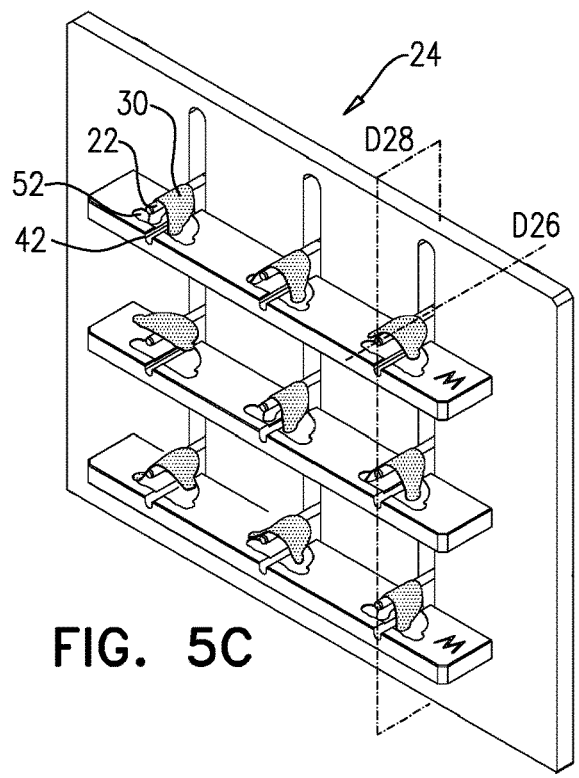

Reference is further made to FIGS. 5B-5C, which are schematic illustrations showing lifting of bars 22 such that each bar supports leaflet 30, with the leaflet draped over the bar, in accordance with some applications of the invention. Typically, and as shown, bar 22 has an initial position (FIG. 5A) with respect to platform 48, in which leaflet 30 may be placeable across the bar such that the leaflet is in contact with upper surface 50, and surface 50 supports the leaflet, e.g., in a flat configuration (FIG. 5B). For example, in the initial position, bar 22 may be disposed below upper surface 50.

For some applications, leaflets 30 are non-isotropically flexible. For example, a leaflet may have a first flexibility when draped over bar 22 with a first side of the leaflet facing up, and a different flexibility when draped over the bar with the opposite side of the leaflet facing up. For such applications, leaflets 30 are typically draped over bars 22 such that they bend in the orientation in which they will bend when in use. Typically, the side of the leaflet that faces up on tester 20 is the side of the leaflet that will face upstream in the functioning prosthetic valve.

For example, leaflets 30 may comprise pericardium that has distinct sides (e.g., a rough side and a smooth side). For such applications, the rough side typically faces upstream in the functioning prosthetic valve. Therefore, for such applications, it may be desirable to orient leaflets 30 upon respective guides 52 with the rough side facing upwards, such that, upon actuation of actuator, each leaflet will drape over respective bar 22 with the rough side facing upwards. Alternatively, it may be desirable to orient leaflets 30 upon respective guides 52 with the smooth side facing upwards, such that, upon actuation of actuator, each leaflet will drape over respective bar 22 with the smooth side facing upwards. It is hypothesized by the inventors that uniform orientation of leaflets 30 upon guide 52 may increase the relevance of leaflet flexibility testing to the performance of the leaflets in the prosthetic valve.

Typically, platform 48 is disposed with respect to bar 22 such that bar-plane D28 bisects guide-outline 54 (FIG. 4B-C). Further typically, and as shown, platform 48 is disposed with respect to bar 22 such that bar-plane D28 bisects guide-outline 54 symmetrically. As shown in FIG. 5C, in the elevated state of tester 20, each bar 22 supports the respective leaflet 30 along the respective bar-axis D26 such that the leaflet drapes over the bar.

For some applications, mount 24 may have a strong color. For some applications, bar-tip 68 may have a second strong color. For some applications, platform 48 may have a third strong color. For example, a platform face 36 of platform 48 may have the third strong color. It is to be noted that the term "strong color" (including the specification and the claims) relates to color saturation. For example, primary colors may serve as the strong colors. The use of respective strong colors for mount 24, bar-tip 68 and/or platform face 36 is hypothesized to facilitate analysis of the image by facilitating distinction between these components and leaflet 30, and between these components and each other.

Figure 6A:
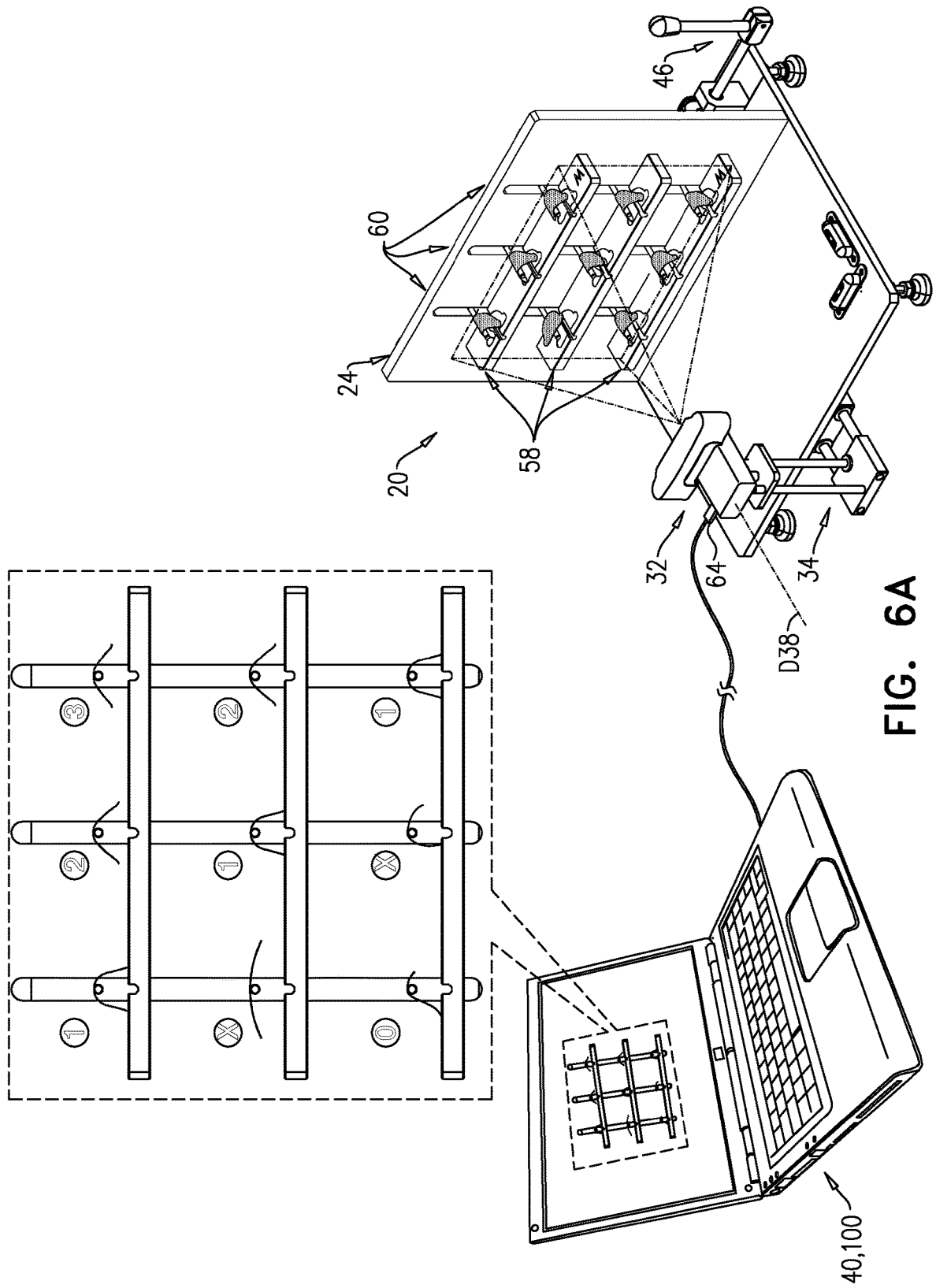
FIGS. 6A-C are schematic illustrations showing use of the tester, in accordance with some applications of the invention.
Figure 6B:
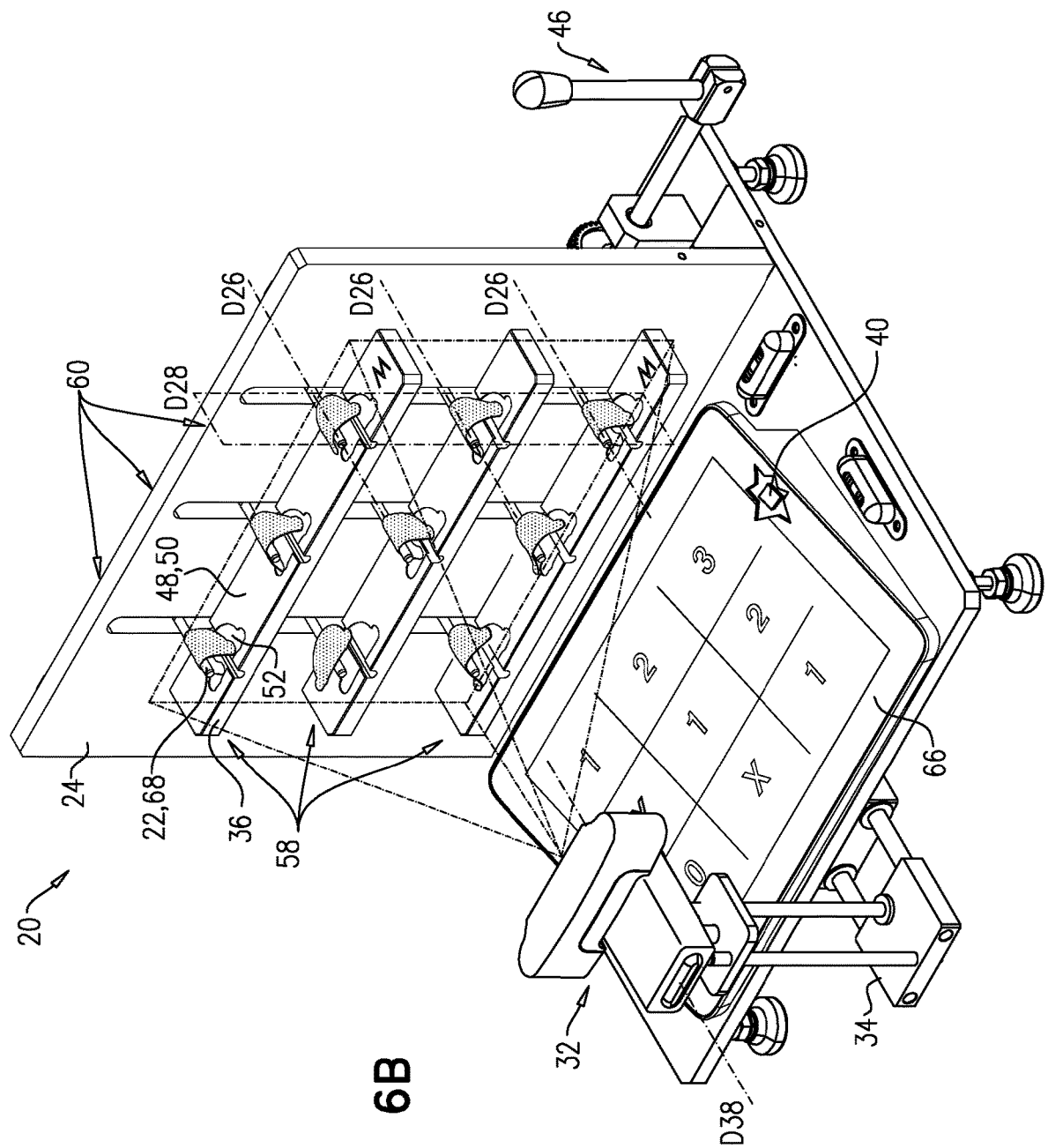
Figure 6C:
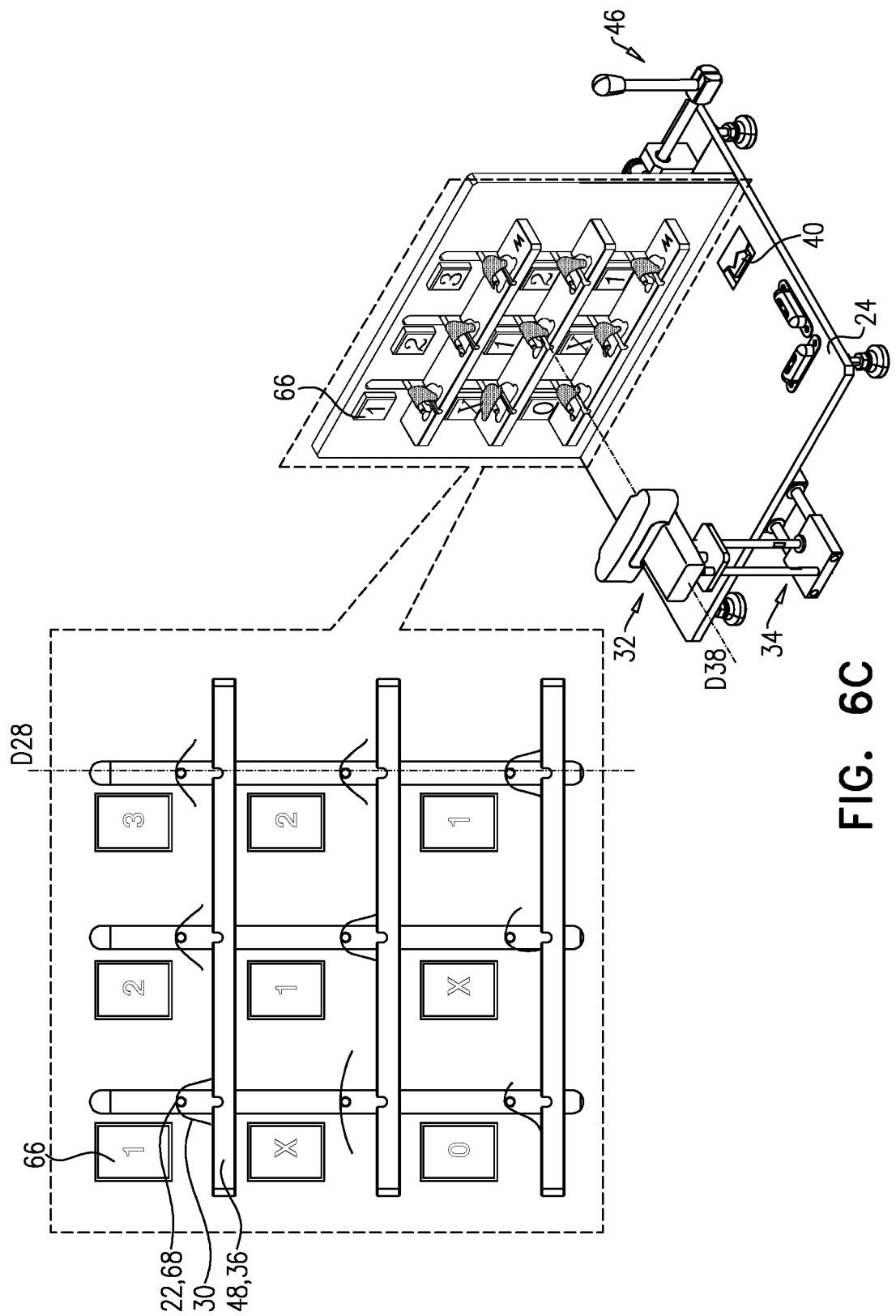

Reference is made to FIGS. 6A-C, which are schematic illustrations showing use of tester 20, in accordance with some applications of the invention.

As described hereinabove, image sensor 32 acquires an image that includes the plurality of leaflets 30 draped over their respective bars.

In some applications (e.g., those shown in FIGS. 6B-C), circuitry 40, configured to receive the image, is coupled to (e.g., mounted on) tester 20. Typically, circuitry 40 is further configured to analyze the image, such that, for each leaflet 30 included in the image, the circuitry derives a corresponding flexibility value that is indicative of flexibility of the leaflet. Derivation of the flexibility value is described in more detail hereinbelow.

For some applications, circuitry 40 is not mounted on tester 20. For such embodiments, tester 20 may include an image output device (e.g., a port or wireless transceiver) 64 (FIG. 6A). Typically, output device 64 is configured to interface with a distinct computer 100 (e.g., a general-purpose computer), and therefore device 64 typically operates according to a recognized standard, such as USB or Bluetooth. For such applications, software is provided to be run on computer 100, and therefore the circuitry of the computer serves as circuitry 40.

For some applications, and as described in more detail hereinbelow, circuitry 40 is further configured to assign a category to each of the leaflets, in response to the flexibility value. Typically, and as shown in FIGS. 6B-C, tester 20 includes at least one indicator 66 that is in communication with circuitry 40, and indicates the respective category assigned to each leaflet 30. For some applications, tester 20 comprises a single indicator (e.g., a display) that indicates the categories of all of the leaflets (e.g., as shown in FIG. 6B). For other applications, tester 20 comprises a respective indicator 66 for each leaflet 30, the indicator configured to indicate the category assigned to the leaflet. For example, indicator 66 may be disposed adjacent to the respective bar 22 that supports the respective leaflet 30 (e.g., as shown in FIG. 6C). For applications in which a distinct computer receives the image and derives the value, the computer (e.g., a display of the computer) also serves as the indicator that indicates the categories (e.g., as shown in FIG. 6A).

For some applications, circuitry 40 is pre-programmed with a calibration routine, such that all leaflets 30 included in the image acquired by sensor 32 are correctly analyzed, e.g., despite each leaflet being disposed at a different position with respect to the image sensor. For some applications, the calibration routine includes acquiring an image that includes all bar-tips 68, and analyzing the image in order to determine a position of sensor 32 with respect to the plurality of bars. For some such applications, the calibration routine is performed automatically, e.g., using the same image that includes the plurality of leaflets, which will be analyzed by circuitry 40 to derive their respective flexibility values, as described hereinbelow.

For some applications, sensor-bracket 34 comprises an electronic actuator, with which circuitry 40 may interface in order to move image sensor 32 (e.g., along sensor-axis D38). For some such applications, this movement is used to facilitate the calibration routine. The calibration of image sensor 32 may adjust a field of view of image sensor 32 such that the image sensor acquires an image that includes all leaflets 30.

Reference is made to FIGS. 7A-C, 8A-B and 9A-B, which are schematic illustrations showing image parameters that may be calculated by circuitry 40 in order to derive a flexibility value, in accordance with some applications of the invention. Circuitry 40 typically derives flexibility values for leaflets 30 by digitally analyzing the image acquired by sensor 32. Circuitry 40 may derive the flexibility values in response to a single image parameter, or a combination of image parameters, e.g., as described hereinbelow.

FIG. 7A shows a leaflet 30a that has high flexibility. FIG. 7B shows a leaflet 30b that has moderate flexibility. FIG. 7C shows a leaflet 30c that has low flexibility.

As described hereinabove, bars 22 are configured to support leaflet 30 along bar-axis D26 such that the leaflet drapes over the bar. As shown, a first-leaflet-tip 70 is disposed below the bar on a first side 72 of the bar, and a second-leaflet-tip 74 is disposed below the bar on a second side 76 of the bar. For example, first-leaflet-tip 70 may be a lowest part of leaflet 30 on first side 72, and second-leaflet-tip 74 may be a lowest part of leaflet 30 on second side 76. In some applications, circuitry 40 is configured to identify, in the acquired image, first-leaflet-tip 70 and second-leaflet tip 74, and to derive the leaflet-flexibility value at least in part responsively to a first-leaflet-tip position D96 of first leaflet tip 70 and a second-leaflet-tip position D98 of second leaflet tip 74.

Image parameters that are calculated by circuitry 40 to derive leaflet-flexibility values may include one or more of the following:

(i) A direct distance D82 between first-leaflet-tip position D96 and second-leaflet-tip position D98. It is to be noted that the term "direct distance" (including the specification and the claims) means the length of a shortest line between two positions (e.g. D82 between D96 and D98, D84 between D96 and bar-tip 68, or D86 between D98 and bar-tip 68).

(ii) An Area Under the Curve (AUC) D80 defined by a leaflet draping-contour line 78 and an AUC closure line D102.

(iii) An axial height D88 or D90 along a vertical axis between (a) first-leaflet-tip position D96 and/or second-leaflet-tip position D98, respectively, and (b) bar-tip 68.

(iv) An axial distance D92 or D94 along a horizontal axis between (a) first-leaflet-tip position D96 or second-leaflet-tip position D98, respectively, and (b) bar-tip 68.

(v) A length of the leaflet draping-contour line 78 (a) between bar-tip 68 and first-leaflet-tip position 96, and (b) between bar-tip 68 and second-leaflet-tip 98.

The use of a plurality of image parameters to derive leaflet-flexibility values is hypothesized by the inventors to more accurately reflect leaflet flexibility than may be derived from a single parameter. For example, a low AUC may alternatively indicate either a highly flexible or highly inflexible leaflet. The integration of AUC with direct distance D82 between first-leaflet-tip position D96 and second-leaflet-tip position D98 may aid in deriving a leaflet-flexibility value that more accurately reflects the leaflet's flexibility.

In some applications, leaflet-flexibility values may be used to facilitate sorting of the leaflets into categories of leaflet flexibility. For example, high-flexibility leaflet 30a may be assigned by tester 20 (e.g., circuitry 40 thereof) to a flexibility category "1", moderate-flexibility leaflet 30b may be assigned to a flexibility category "2", and low-flexibility leaflet 30c may be assigned to a flexibility category "3"—and the user may sort the leaflets according to the assigned categories. As described hereinabove, the category for each leaflet is typically indicated by indicator 66, e.g., as shown in FIGS. 6A-C.

For some applications, the user may sort leaflets 30 according to the assigned category—e.g., into receptacles corresponding to each flexibility category. Leaflets 30 may also be assigned to a "retest" category, or a "discard" category, e.g., as described herein below. Typically, the process is a batch process, in which multiple leaflets are placed on tester 20, tested, and then sorted.

Leaflets that are assigned to the "retest" category may be resituated within the same or a different guide 52 for retesting (e.g., in the subsequent batch). Alternatively, leaflets 30 assigned to a "retest" category may be collected into a "retest" receptacle for subsequent retesting (e.g., in a dedicated retesting batch).

Reference is also made to FIGS. 11A-B, which are graphs representing a relationship between leaflet-flexibility values of a set of leaflets 30, and the leaflet-flexibility categories or groups to which the same leaflets are assigned, in accordance with some applications of the invention. As described hereinabove, for some applications leaflets 30 are assigned to leaflet-flexibility categories, based upon leaflet-flexibility values. Leaflet-flexibility categories are typically categorical variables. For example, the categories may be named categories "1", "2" and "3", e.g., as described hereinabove. Leaflet-flexibility values are typically continuous numerical variables. For example, leaflet-flexibility values may span a range from 10 to 40, as shown.

Typically, and as shown, each leaflet flexibility category is defined by threshold leaflet-flexibility values, each threshold leaflet-flexibility value lying at a respective extreme of the category, such that each category includes leaflets with values spanning a range between the upper and lower thresholds of the category. For example, FIG. 11A shows category 1 spanning a range D148 of flexibility values, category 2 spanning a range D146 of flexibility values, and category 3 spanning a range D144 of flexibility values. Solid vertical lines represent the thresholds dividing between the leaflet-flexibility categories. For example, category "3" spans a range of leaflet-flexibility values between threshold D106 and threshold D112 ranging between 10 and 20, category "2" spans a range of leaflet-flexibility values between threshold D112 and threshold D118 ranging between 20 and 30, and category "1" spans a range of leaflet-flexibility values between threshold D118 and threshold D124 ranging between 30 and 40.

It is to be noted that the leaflet-flexibility values and leaflet-flexibility category thresholds shown in FIGS. 11A-B are for illustrative purposes only. The values, ranges, and thresholds are arbitrary, and are not intended to exclude alternate leaflet-flexibility values, ranges, or thresholds.

In FIGS. 11A-B, hollow circles 138, 140 and 142 represent three leaflets that would be assigned to leaflet-flexibility category 1, having leaflet-flexibility values spanning a range from 30 to 40; hollow circles 132, 134 and 136 represent three leaflets that would be assigned to leaflet-flexibility category 2, having leaflet-flexibility values spanning a range from 20 to 30; and hollow circles 126, 128 and 130 represent three leaflets that would be assigned to leaflet-flexibility category 3, having leaflet-flexibility values spanning a range from 10 to 20.

It is hypothesized by the inventors that assigning leaflets 30 to flexibility categories may enable efficient sorting of leaflets by their flexibility values. However, for some applications, sorting leaflets purely by such a categorization technique may result in leaflets that do not necessarily have the most similar flexibility values, being sorted into the same category. For instance, FIG. 11A shows the flexibility value of leaflet 130 (which would be categorized into category "3") to be closest to that of leaflets 132 and 134 (which would be categorized into category "2"). This potential obscuring of the similarity between leaflets in different categories due to their similar flexibility values being on different sides of a category threshold value is referred to herein as "threshold artifact." Alternative or complimentary strategies to account for threshold artifact when assigning leaflets to flexibility categories, are described below.

For some applications, circuitry 40 is configured to refer certain leaflets 30 for manual assignment (e.g., by a human specialist) to flexibility categories. For some applications, circuitry 40 may designate leaflets 30 with flexibility values that are particularly close to the threshold values, to transition categories. For example, circuitry 40 may be configured such that each threshold has a margin, and leaflets whose flexibility values fall within a margin of a threshold are assigned to a transition category. FIG. 11A further shows dotted vertical margin lines demarcating margins of respective thresholds: D108 demarcates an upper margin 150 of threshold D106, D110 demarcates a lower margin of threshold D112, D114 demarcates an upper margin 154 of threshold D106, D116 demarcates a lower margin of threshold D118, D120 demarcates an upper margin of threshold D118, and D122 demarcates a lower margin of threshold D124. For example, in FIG. 11A the leaflets represented by symbols 130, 132, and 134 fall within such margins, and are therefore designated to transition categories. Leaflets designated to transition categories, referred to as "transition category leaflets" (e.g., category "1-2", category "2-3", or category "3-x"), may then be referred to a person (e.g., a specialist) in order to be assigned manually to a flexibility category.

For some applications, and as shown, circuitry 40 is not configured with a lower margin for threshold D106 and/or an upper margin of threshold D124. For some such applications, leaflets whose flexibility value falls below threshold D106 or above threshold D124 are referred to a person in order to be manually assessed (e.g., to be manually assigned to a flexibility category). For some such applications, such leaflets are automatically assigned to the corresponding "discard" category "x" or "y", e.g., to increase efficiency by reducing the likelihood of an unsuitable leaflet being referred to a specialist for manual categorization. For some such applications, leaflets whose flexibility value falls below threshold D106 are referred to a person in order to be manually assessed, whereas leaflets whose flexibility value falls above threshold D124 are automatically assigned to the corresponding "discard" category. For some such applications, leaflets whose flexibility value falls above threshold D124 are referred to a person in order to be manually assessed, whereas leaflets whose flexibility value falls below threshold D106 are automatically assigned to the corresponding "discard" category.

Alternatively, circuitry 40 is configured with a lower margin for threshold D106 and/or an upper margin of threshold D124, e.g., similarly to the margins of the other thresholds.

For some applications, tester 20 may simply indicate that a particular leaflet requires manual categorization. For some applications, tester 20 may facilitate manual categorization by indicating the categories between which the leaflet's flexibility value falls. For example, indicator 66 of tester 20 may display "2-3" for a leaflet whose flexibility value falls within margin 152 of the lower threshold of category 2 or within margin 154 of the upper threshold of category 3.

For some applications, transition category leaflets may be designated to be tested a second time. It is hypothesized by the inventors that: 1) manual assignment of transition category leaflets to flexibility categories, and/or 2) retesting of transition category leaflets, may increase the validity and clinical utility of leaflet flexibility categories to which leaflets 30 are assigned.

For some applications, leaflets may be grouped by circuitry 40 and/or by user according to similarity of flexibility values, e.g., without the use of flexibility categories. Leaflets 30 of the same group may then be included together in an individual prosthetic heart valve. Circuitry 40 may therefore group leaflets 30 into groups of a desirable size (e.g., groups of two leaflets for a bileaflet valve, or groups of three leaflets for a trileaflet valve). For example, in FIG. 11B, ovals 166 and 168 indicate such grouping. Oval 168 indicates a group of three leaflets (138, 140 and 142), which would all have been assigned to the same category (category 1) had the categorization technique had been used (e.g., as shown in FIG. 11A). In this case, grouping these three leaflets 30 according to similarity of their respective leaflet-flexibility values would yield a similar result to that of sorting the leaflets into leaflet-flexibility categories.

That is, for some applications of the invention, tester 20 (e.g., circuitry 40 thereof) is configured to group leaflets 30 (e.g., all of the leaflets that are on tester 20) into groups, based on similarity between (i) the flexibility value of each leaflet of the plurality of leaflets, and (ii) the flexibility value of other leaflets of the plurality of leaflets, each of the groups including a predetermined number of leaflets.

In contrast, oval 166 indicates a group of three leaflets (130, 132 and 134), in which two of the leaflets (132 and 134) would have been assigned to one category (category 2), and one of the leaflets (130) would have been assigned to a different category (category 3), had the categorization technique had been used (e.g., as shown in FIG. 11A). Grouping these three leaflets 30 be included together in an individual prosthetic heart valve would yield a prosthetic heart valve with leaflets having more similar leaflet-flexibility values than would a prosthetic heart valve with leaflets sorted into category 3 or into category 2.

Figure 10:
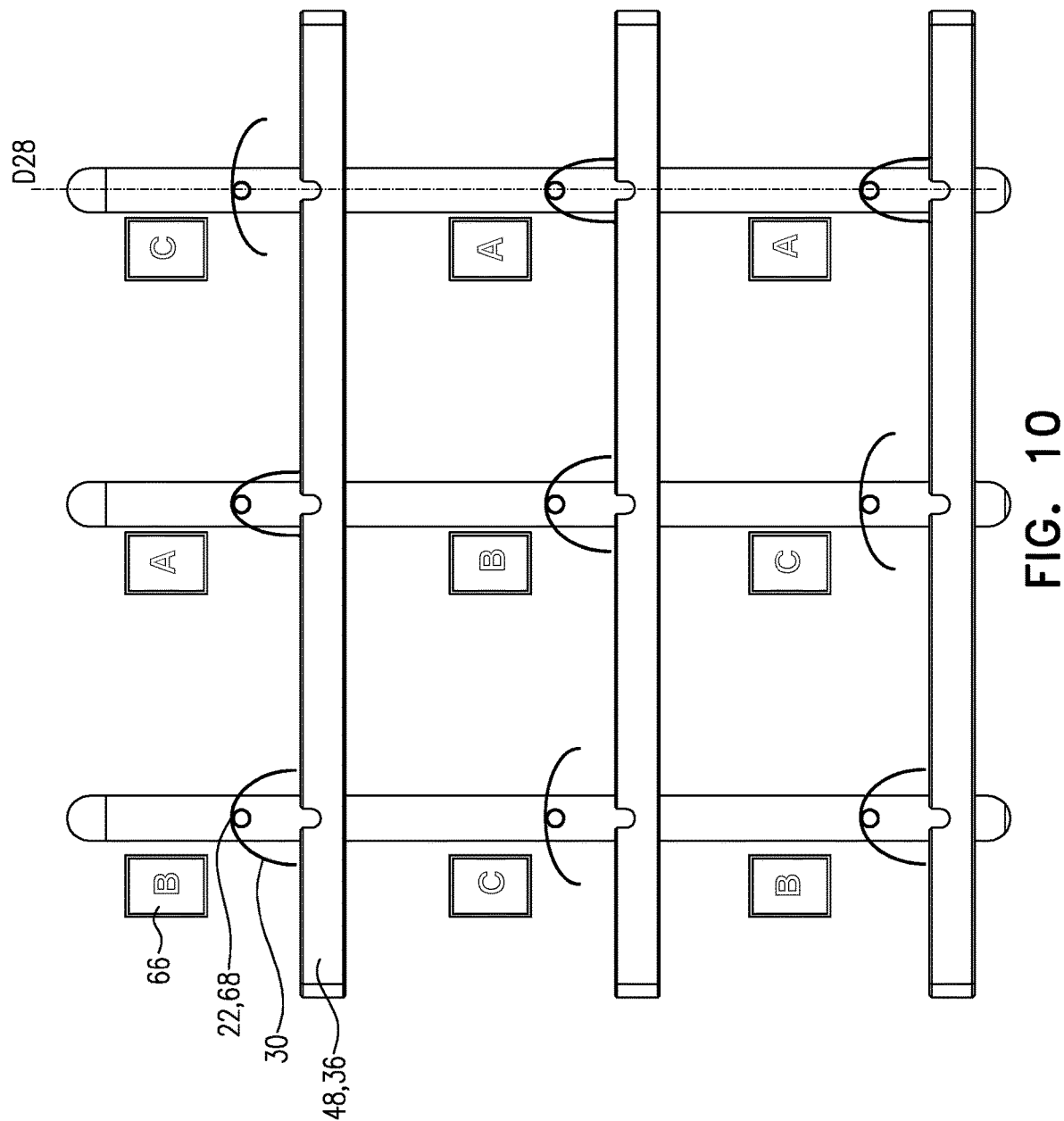
FIG. 10 is a schematic illustration of the tester using leaflet-flexibility values to group leaflets, in accordance with some applications of the invention.

Reference is also made to FIG. 10, which is a schematic illustration of tester 20 using leaflet-flexibility values to group leaflets 30, in accordance with some applications of the invention. FIG. 10 shows leaflets 30 draped over bars 22, and indicators 66 indicating the grouping of leaflets into groups "A", "B" and "C" according to similarity of their respective leaflet-flexibility values. In the example shown, the simultaneous testing of nine leaflets, and the grouping of nine leaflets into three groups, may enable the construction of three trileaflet prosthetic heart valves, from each testing session. In the example shown, one trileaflet valve would be constructed from the three leaflets in group A, one trileaflet valve from those in group B, and one trileaflet valve from those in group C. It is hypothesized by the inventors that grouping leaflets 30 with similar leaflet-flexibility values (e.g., to be sewn together in a prosthetic heart valve) may facilitate the preparation of properly functioning prosthetic heart valves.

For some applications, leaflets 30 are first assigned to categories, and subsequently grouped into groups. For such applications, (i) leaflets 30 are placed onto tester 20, tested according to the categorization technique, and sorted according to their categories—e.g., into collections, and (ii) subsequently, leaflets from a single category are re-placed onto tester 20 and retested according to the grouping technique. It is hypothesized by the inventors that the grouping of leaflets 30 assigned to the same leaflet flexibility category, according to their flexibility values, may enable grouping of leaflets into groups of highly similar flexibility. FIGS. 8A-B are schematic illustrations of unsuitable leaflets, in accordance with some applications of the invention. FIG. 8A schematically illustrates a leaflet 30d that is insufficiently flexible for use in a prosthetic heart valve. In response to the derived flexibility value, circuitry 40 typically assigns the leaflet to an appropriate category (e.g., an "unsuitable" or "discard" category). This is represented in FIGS. 6A-C as category "x." For example, FIG. 11A shows category "x" spanning a range D162 of flexibility values, range D162 being separated from range D144 of flexibility values of category "3" by threshold D106. Leaflet-flexibility values within range D162 may characterize leaflets unsuitable for use in a prosthetic heart valve. Although FIGS. 6A-C depict unsuitable category "x" leaflets that are unsuitable for being overly inflexible, this depiction is not meant to exclude the possibility that excessively flexible leaflets may be assigned to an alternate category "y" of excessively flexible leaflets. For example, FIG. 11A shows category "y" spanning a range D164 of flexibility values, range D164 being separated from range D148 of flexibility values of category "1" by threshold D124. Leaflet-flexibility values within range D164 may characterize leaflets unsuitable for use in a prosthetic heart valve. Typically, unsuitable leaflets assigned to either category "x" or "y" 30 are discarded.

It is to be noted that, although leaflets 30 in FIGS. 7A-C and FIG. 8A drape symmetrically, the scope of the invention includes deriving leaflet-flexibility values and/or assigning categories for a leaflet that drapes asymmetrically, at least up to a certain degree of asymmetry. FIG. 8B shows a non-isotropically-flexible leaflet 30e that drapes asymmetrically as a result of its non-isotropic flexibility. Circuitry 40 may be configured to categorize non-isotropically-flexible leaflets as described hereinabove, at least up to a threshold degree of asymmetric draping. For some applications, for a leaflet whose draping asymmetry is greater than a threshold degree of asymmetry, circuitry 40 may assign the leaflet to an appropriate category (e.g., an "unsuitable" or "discard" category), such as category "x" described hereinabove.

For some applications, circuitry 40 identifies non-isotropic flexibility of a leaflet 30 by calculating a difference between axial distance D92 and axial distance D94. Alternatively or additionally, circuitry 40 may identify non-isotropic flexibility of a leaflet 30 by calculating a difference between axial distance D88 axial distance D90. It is hypothesized by the inventors that a difference between D92 and D94, and/or a difference between D88 and D90, will be greater for non-isotropically-flexible leaflets than for isotropically-flexible leaflets, thereby facilitating identification of non-isotropically-flexible leaflets.

As described hereinabove, circuitry 40 may be configured to detect asymmetric draping. In that case, the asymmetric draping is asymmetric draping that is caused by, and is indicative of, non-isotropic flexibility of the leaflet. Circuitry 40 may also be configured to detect asymmetric draping that is caused by, and is indicative of, improper positioning of the leaflet being tested, e.g., caused by the user improperly positioning the leaflet, and/or by slippage of the leaflet during elevation of the bar. In response to detection of such improper positioning, circuitry 40 typically assigns the leaflet to a "retest" category.

An exemplary reason for a leaflet to be assigned to the "retest" category is measurement error. In this context, the term "measurement error" is used to refer to situations in which image parameters and/or leaflet-flexibility values may not enable circuitry 40 to accurately assign leaflet 30 to a leaflet flexibility category. In such cases, indicator 66 may indicate a need to repeat the measurement and/or to adjust leaflet flexibility measurement conditions. For example, FIGS. 9A-B show two types of measurement error, in which leaflets 30 may be assigned to the "retest" category that indicates a need to retest the leaflets. This is represented by a "0" in FIGS. 6A-C.

FIG. 9A shows measurement error introduced by suboptimal positioning of leaflet 30 on bar 22. Another potential source of measurement error may be adherence of leaflet 30 to guide 52, shown in FIG. 9B, which may cause slippage of the leaflet over the bar during elevation of the bar. FIG. 9B shows an adhesion site 104 at which leaflet 30 had adhered to platform 48 (e.g., guide 52 thereof), such that when bar 22 was elevated, the leaflet was pulled off of the bar to one side. Measurement error may be identified in response to a difference between (i) a direct distance D84 between first-leaflet-tip position D96 and bar-tip 68, and (ii) a direct distance D86 between second-leaflet-tip position D98 and the bar-tip. It is hypothesized by the inventors that the difference between direct distances D84 and D86 may be greater when leaflet 30 is improperly positioned and/or has slipped. It is further hypothesized by the inventors that the difference between direct distances D84 and D86 is more strongly correlated with measurement error than with non-isotropic flexibility of a leaflet, facilitating discrimination between measurement error and proper measurement of leaflet flexibility.

For some applications, measurement error is identified in response to a difference between vertical axial distance d88 and vertical axial distance d90. For some applications, measurement error is identified in response to a difference between horizontal axial distance d92 and horizontal axial distance d94.

For some applications, circuitry 40 may detect instances of measurement error in response to a plurality of image parameters to, e.g., by cross-validation of image parameters. For example, circuitry 40 may compare a difference between D88 and D90, to a difference between D92 and D94. Alternatively or additionally, circuitry 40 may compare a difference between D88 and D92, to a difference between D90 and D94. In addition to one or both of these comparisons, circuitry 40 may also take into account direct distances D84 and D86. It is hypothesized by the inventors that the derivation of leaflet-flexibility values in response to more than one image parameter advantageously facilitates identifying measurement errors, e.g., distinguishing between (i) asymmetric draping caused by measurement error, and (ii) asymmetric draping caused by non-isotropic flexibility.

The use of a plurality of image parameters to derive leaflet-flexibility values is therefore hypothesized by the inventors to increase the validity and clinical utility of the flexibility categories to which leaflets 30 are assigned.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for testing a plurality of prosthetic heart valve leaflets, the apparatus comprising:
a vertical mount;
a plurality of horizontal bars movably coupled to the mount, each bar extending away from the mount toward a bar-tip, along a respective bar-axis that lies on a respective vertical bar-plane, and each bar configured to support a respective leaflet along the respective bar-axis such that the respective leaflet drapes over the respective bar such that a first-leaflet-tip is disposed below the bar on a first side of the bar, and a second-leaflet-tip is disposed below the bar on a second side of the bar;
an image sensor, positioned opposite the mount, facing the bar-tips of the plurality of bars and the mount so as to be oriented to acquire an image that includes the plurality of leaflets draped over the plurality of bars; and circuitry, configured to receive the image, and to analyze the image, wherein the analysis of the image is such that, for each of the leaflets included in the image, the circuitry:
  identifies the first-leaflet-tip and the second-leaflet tip, and
  derives a corresponding flexibility value that is indicative of flexibility of the leaflet, at least in part responsively to a direct distance between a first-leaflet-tip position of the first leaflet tip and a second-leaflet-tip position of the second leaflet tip.

2. The apparatus according to claim 1, wherein the mount is generally flat, and the plurality of horizontal bars are generally parallel with each other.

3. The apparatus according to claim 1, wherein the mount is concave toward the image sensor.

4. The apparatus according to claim 1, comprising exactly one image sensor.

5. The apparatus according to claim 1, further comprising an image output device configured to transmit the image.

6. The apparatus according to claim 1, further comprising a sensor-bracket that movably couples the image sensor to the mount, such that the image sensor is movable along a sensor-axis with respect to the mount.

7. The apparatus according to claim 1, wherein the circuitry is configured to, for each of the leaflets, identify a draping-contour line, and to derive the flexibility value at least in part responsively to an Area Under Curve value defined by the draping-contour line.

8. The apparatus according to claim 1, wherein the circuitry is configured to assign a respective flexibility category to each of the leaflets, responsively to the flexibility value.

9. The apparatus according to claim 8, further comprising at least one indicator that is in communication with the circuitry, the indicator configured to indicate the respective category assigned to each leaflet.

10. The apparatus according to claim 8, wherein the apparatus comprises a respective indicator for each of the leaflets, each of the indicators being configured to indicate the respective category assigned to the respective leaflet.

11. The apparatus according to claim 10, wherein each of the indicators is disposed adjacent to the respective bar that supports the respective leaflet.

12. The apparatus according to claim 8, wherein
each flexibility category has an upper flexibility-value threshold and a lower flexibility-value threshold, and the circuitry is configured:
  to assign a respective flexibility category to each leaflet, responsively to the flexibility value of the leaflet falling between the upper flexibility-value threshold and the lower flexibility-value threshold for the category, and
  for a leaflet that has a flexibility value that falls within a margin of a threshold value, to indicate a recommendation that the leaflet be manually assigned to a flexibility category.

13. The apparatus according to claim 1, wherein the circuitry is configured to derive the value at least in part responsively to:
  a direct distance between the first-leaflet-tip position and the bar-tip of the respective bar, and
  a direct distance between the second-leaflet-tip position and the bar-tip of the respective bar.

14. The apparatus according to claim 1, wherein the mount is a strong color.

15. The apparatus according to claim 14, further comprising:
  a platform having an upper surface, the platform coupled to the mount such that the bar-plane intersects the platform; and
  an actuator, actuation of the actuator moving each of the bars vertically, in the respective bar-plane, with respect to the platform, wherein:
  the strong color of the mount is a first strong color, and
  the platform is a second strong color that is distinct from the first strong color.

16. The apparatus according to claim 14, wherein:
the strong color of the mount is a first strong color, and
each of the bars has an end, at least the end of the bar being a second strong color that is distinct from the first strong color.

17. Apparatus for testing a plurality of prosthetic heart valve leaflets, the apparatus comprising:
  a vertical mount;
  a plurality of horizontal bars movably coupled to the mount, each bar extending away from the mount along a respective bar-axis that lies on a respective vertical bar-plane, and each bar configured to support a respective leaflet along the respective bar-axis such that the respective leaflet drapes over the respective bar;
  an image sensor, positioned opposite the mount, facing the plurality of bars and the mount so as to be oriented to acquire an image that includes the plurality of leaflets draped over the plurality of bars; and
  circuitry, the configured to:
    receive the image,
    analyze the image, the analysis of the image being such that, for each of the leaflets included in the image, the circuitry derives a corresponding flexibility value that is indicative of flexibility of the leaflet, and
    group the leaflets into groups, based on similarity between (i) the flexibility value of each leaflet of the plurality of leaflets, and (ii) the respective flexibility value of other leaflets of the plurality of leaflets, each of the groups including a predetermined number of leaflets.

18. The apparatus according to claim 17, wherein the predetermined number of leaflets in each group is two leaflets.

19. The apparatus according to claim 17, wherein the predetermined number of leaflets in each group is three leaflets.

20. The apparatus according to claim 17, further comprising at least one indicator that is in communication with the circuitry, the indicator configured to indicate the respective group to which each leaflet is grouped.

21. The apparatus according to claim 17, wherein the apparatus comprises a respective indicator for each of the leaflets, each of the indicators being configured to indicate the respective group to which each leaflet is grouped.

22. The apparatus according to claim 21, wherein each of the indicators is disposed adjacent to the respective bar that supports the respective leaflet.

23. The apparatus according to claim 17, wherein the mount is generally flat, and the plurality of horizontal bars are generally parallel with each other.

24. The apparatus according to claim 17, wherein the mount is concave toward the image sensor.

25. The apparatus according to claim 17, comprising exactly one image sensor.

26. The apparatus according to claim 17, further comprising an image output device configured to transmit the image.

27. The apparatus according to claim 17, further comprising a sensor-bracket that movably couples the image sensor to the mount, such that the image sensor is movable along a sensor-axis with respect to the mount.

28. The apparatus according to claim 17, wherein the circuitry is configured to, for each of the leaflets, identify a draping-contour line, and to derive the flexibility value at least in part responsively to an Area Under Curve value defined by the draping-contour line.

29. The apparatus according to claim 17, wherein:
each of the bars extends away from the mount towards a respective bar-tip, and
each of the bars is configured to support a respective leaflet along the respective bar-axis such that the respective leaflet drapes over the respective bar such that a first-leaflet-tip is disposed below the bar on a first side of the bar, and a second-leaflet-tip is disposed below the bar on a second side of the bar.

30. The apparatus according to claim 29, wherein the circuitry is configured to identify the first-leaflet-tip and the second-leaflet tip, and to derive the value at least in part responsively to a first-leaflet-tip position of the first leaflet tip and a second-leaflet-tip position of the second leaflet tip.

31. The apparatus according to claim 30, wherein the circuitry is configured to derive the value at least in part responsively to a vertical height of the first-leaflet-tip position and a vertical height of the second-leaflet-tip position.

32. The apparatus according to claim 30, wherein the circuitry is configured to derive the value at least in part responsively to a horizontal location of the first-leaflet-tip position and a horizontal location of the second-leaflet-tip position.

33. The apparatus according to claim 30, wherein the circuitry is configured to derive the value at least in part responsively to:
a direct distance between the first-leaflet-tip position and the bar-tip of the respective bar, and
a direct distance between the second-leaflet-tip position and the bar-tip of the respective bar.

34. The apparatus according to claim 30, wherein the circuitry is configured to derive the value at least in part responsively to a direct distance between the first-leaflet-tip position and the second-leaflet-tip position.

35. The apparatus according to claim 17, further comprising:
a platform having an upper surface, the platform coupled to the mount such that the bar-plane intersects the platform; and
an actuator, actuation of the actuator moving the bar vertically, in the bar-plane, with respect to the platform.

36. The apparatus according to claim 35, wherein the bar has an initial position with respect to the platform, in which the leaflet is placeable across the bar such that the leaflet is in contact with the surface.

37. The apparatus according to claim 36, wherein, in the initial position, the bar is disposed below the surface.

38. The apparatus according to claim 35, wherein the platform has a guide that defines a guide-outline that corresponds to a leaflet-outline of the leaflet, such that when the leaflet is placed on the surface with the leaflet-outline aligned with the guide-outline, the leaflet is disposed across the bar.

39. The apparatus according to claim 38, wherein the platform is disposed with respect to the bar such that the bar-plane bisects the guide-outline.

40. The apparatus according to claim 39, wherein the platform is disposed with respect to the bar such that the bar-plane bisects the guide-outline symmetrically.

41. The apparatus according to claim 38, wherein the surface of the guide is at least partially comprised of a low-friction material.

42. The apparatus according to claim 41, wherein the low-friction material is Teflon.

43. The apparatus according to claim 41, wherein the bars extend away from the mount in parallel with each other.

44. The apparatus according to claim 41, wherein the bars are arranged, with respect to the mount, in multiple rows and multiple columns.

45. The apparatus according to claim 17, wherein the mount is a strong color.

46. The apparatus according to claim 45, further comprising:
a platform having an upper surface, the platform coupled to the mount such that the bar-plane intersects the platform; and
an actuator, actuation of the actuator moving each of the bars vertically, in the respective bar-plane, with respect to the platform, wherein:
the strong color of the mount is a first strong color, and
the platform is a second strong color that is distinct from the first strong color.

47. The apparatus according to claim 45, wherein:
the strong color of the mount is a first strong color, and
each of the bars has an end, at least the end of the bar being a second strong color that is distinct from the first strong color.

48. Apparatus for testing a plurality of prosthetic heart valve leaflets, the apparatus comprising:
a vertical mount;
a plurality of horizontal bars movably coupled to the mount, each bar extending away from the mount along a respective bar-axis that lies on a respective vertical bar-plane, and each bar configured to support a respective leaflet along the respective bar-axis such that the respective leaflet drapes over the respective bar; and
an image sensor, positioned opposite the mount, facing the plurality of bars and the mount so as to be oriented to acquire an image that includes the plurality of leaflets draped over the plurality of bars;
a platform having an upper surface, the platform coupled to the mount such that the bar-plane intersects the platform; and
an actuator, actuation of the actuator moving each of the bars vertically, in the bar-plane, with respect to the platform;
wherein each of the bars has a respective initial position with respect to the platform, in which a respective leaflet is placeable across the respective bar such that the leaflet is in contact with the surface.

49. The apparatus according to claim 48, wherein, in the initial position, each bar is disposed below the surface.

50. The apparatus according to claim 48, wherein for each of the bars, the platform has a respective guide that defines a guide-outline that corresponds to a leaflet-outline of the respective leaflet, such that when the respective leaflet is placed on the surface with the leaflet-outline aligned with the guide-outline, the respective leaflet is disposed across the respective bar.

51. The apparatus according to claim 50, wherein the platform is disposed with respect to the bars such that, for each of the bars, the bar-plane bisects the respective guide-outline.

52. The apparatus according to claim 51, wherein the platform is disposed with respect to the bars such that, for each of the bars, the bar-plane bisects the respective guide-outline symmetrically.

53. The apparatus according to claim 50, wherein the surface of the guide is at least partially comprised of a low-friction material.

54. The apparatus according to claim 53, wherein the low-friction material is Teflon.

55. The apparatus according to claim 53, wherein the bars extend away from the mount in parallel with each other.

56. The apparatus according to claim 53, wherein the bars are arranged, with respect to the mount, in multiple rows and multiple columns.

57. The apparatus according to claim 48, wherein the mount is generally flat, and the plurality of horizontal bars are generally parallel with each other.

58. The apparatus according to claim 48, wherein the mount is concave toward the image sensor.

59. The apparatus according to claim 48, comprising exactly one image sensor.

60. The apparatus according to claim 48, further comprising an image output device configured to transmit the image.

61. The apparatus according to claim 48, further comprising a sensor-bracket that movably couples the image sensor to the mount, such that the image sensor is movable along a sensor-axis with respect to the mount.

62. The apparatus according to claim 48, further comprising circuitry, configured to receive the image, and to analyze the image, the analysis of the image being such that, for each of the leaflets included in the image, the circuitry derives a corresponding flexibility value that is indicative of flexibility of the leaflet.

63. The apparatus according to claim 62, wherein the circuitry is configured to, for each of the leaflets, identify a draping-contour line, and to derive the flexibility value at least in part responsively to an Area Under Curve value defined by the draping-contour line.

64. The apparatus according to claim 62, wherein the circuitry is configured to assign a respective flexibility category to each of the leaflets, responsively to the flexibility value.

65. The apparatus according to claim 64, further comprising at least one indicator that is in communication with the circuitry, the indicator configured to indicate the respective category assigned to each leaflet.

66. The apparatus according to claim 64, wherein the apparatus comprises a respective indicator for each of the leaflets, each of the indicators being configured to indicate the respective category assigned to the respective leaflet.

67. The apparatus according to claim 66, wherein each of the indicators is disposed adjacent to the respective bar that supports the respective leaflet.

68. The apparatus according to claim 64, wherein:
each flexibility category has an upper flexibility-value threshold and a lower flexibility-value threshold, and
the circuitry is configured:
to assign a respective flexibility category to each leaflet, responsively to the flexibility value of the leaflet falling between the upper flexibility-value threshold and the lower flexibility-value threshold for the category, and
for a leaflet that has a flexibility value that falls within a margin of a threshold value, to indicate a recommendation that the leaflet be manually assigned to a flexibility category.

69. The apparatus according to claim 62, wherein:
each of the bars extends away from the mount towards a respective bar-tip, and
each of the bars is configured to support a respective leaflet along the respective bar-axis such that the respective leaflet drapes over the respective bar such that a first-leaflet-tip is disposed below the bar on a first side of the bar, and a second-leaflet-tip is disposed below the bar on a second side of the bar.

70. The apparatus according to claim 69, wherein the circuitry is configured to identify the first-leaflet-tip and the second-leaflet tip, and to derive the value at least in part responsively to a first-leaflet-tip position of the first leaflet tip and a second-leaflet-tip position of the second leaflet tip.

71. The apparatus according to claim 70, wherein the circuitry is configured to derive the value at least in part responsively to a vertical height of the first-leaflet-tip position and a vertical height of the second-leaflet-tip position.

72. The apparatus according to claim 70, wherein the circuitry is configured to derive the value at least in part responsively to a horizontal location of the first-leaflet-tip position and a horizontal location of the second-leaflet-tip position.

73. The apparatus according to claim 70, wherein the circuitry is configured to derive the value at least in part responsively to:
a direct distance between the first-leaflet-tip position and the bar-tip of the respective bar, and
a direct distance between the second-leaflet-tip position and the bar-tip of the respective bar.

74. The apparatus according to claim 70, wherein the circuitry is configured to derive the value at least in part responsively to a direct distance between the first-leaflet-tip position and the second-leaflet-tip position.

75. The apparatus according to claim 48, wherein the mount is a strong color.

76. The apparatus according to claim 75, further comprising:
a platform having an upper surface, the platform coupled to the mount such that the bar-plane intersects the platform; and
an actuator, actuation of the actuator moving each of the bars vertically, in the respective bar-plane, with respect to the platform, wherein:
the strong color of the mount is a first strong color, and
the platform is a second strong color that is distinct from the first strong color.

77. The apparatus according to claim 75, wherein:
the strong color of the mount is a first strong color, and
each of the bars has an end, at least the end of the bar being a second strong color that is distinct from the first strong color.

* * * * *